(12) United States Patent
Rosemberg et al.

(10) Patent No.: US 7,021,122 B1
(45) Date of Patent: Apr. 4, 2006

(54) DEVICE FOR THE DETERMINATION OF BLOOD CLOTTING BY CAPACITANCE OR RESISTANCE

(75) Inventors: Yossef Rosemberg, Raanana (IL); Falk Fish, Tel Aviv (IL); Raphael Levi, Yehud (IL)

(73) Assignee: Orgenics Biosensors Ltd., Yavne (IL)

( * ) Notice: Subject to any disclaimer, the term of this patent is extended or adjusted under 35 U.S.C. 154(b) by 0 days.

(21) Appl. No.: 09/646,348

(22) PCT Filed: Mar. 18, 1999

(86) PCT No.: PCT/IL99/00156

§ 371 (c)(1),
(2), (4) Date: Dec. 8, 2000

(87) PCT Pub. No.: WO99/47907

PCT Pub. Date: Sep. 23, 1999

(30) Foreign Application Priority Data

Mar. 18, 1998 (IL) ..................................... 123757
Oct. 23, 1998 (IL) ..................................... 126738

(51) Int. Cl.
*G01N 11/00* (2006.01)
(52) U.S. Cl. .................... 73/54.01; 73/304 C
(58) Field of Classification Search ............. 73/290 R, 73/304 C, 54.01
See application file for complete search history.

(56) References Cited

U.S. PATENT DOCUMENTS

| 3,674,012 A | * | 7/1972 | Sage | 600/369 |
| 3,699,437 A | * | 10/1972 | Ur | 324/722 |
| 3,753,092 A | * | 8/1973 | Ludlow et al. | 324/663 |
| 3,840,806 A | | 10/1974 | Stoner et al. | |
| 3,951,606 A | | 4/1976 | Moyer et al. | |
| 4,301,412 A | | 11/1981 | Hill et al. | |

(Continued)

FOREIGN PATENT DOCUMENTS

WO    WO 94/16095    1/1994

(Continued)

*Primary Examiner*—Hezron Williams
*Assistant Examiner*—Rodney Frank
(74) *Attorney, Agent, or Firm*—Mark M. Friedman

(57) ABSTRACT

A sensor device (10) and a method for measuring a viscosity of a sample of a liquid. The sensor features a chamber (12) for receiving the sample of the liquid, two electrodes (18) disposed either on the surfaces of the chamber, but possibly isolated from contacting the sample, or electrodes located externally to the chamber, and a capacitance measuring circuit (25). The sensor is used by connecting to a measurer for determining a capacitance on the electrodes, such that the capacitance directly reflects a volume occupied by the sample of the liquid. Preferably, the liquid is blood and the capacitance is used to determine the clotting time of the blood. Also preferably, a cover for the chamber is provided with at least one aperture, which more preferably is a mesh. Alternatively, an electrical property such as the amplitude of current passed through the sample is used to determine clotting time. Also preferably, the time period required for the maximum capacitance to be reached could be measured. Alternatively, the capacitance could be measured after a fixed time period (34) had elapsed. Also alternatively, the time period required for the maximum current to be reached could be measured, or the amount of current could be measured after a fixed time period had elapsed. In preferred embodiments of the present invention, a kit for measuring the clotting time of blood is provided. In other preferred embodiments of the present invention, methods are provided for using the kit and device of the present invention.

40 Claims, 18 Drawing Sheets

U.S. PATENT DOCUMENTS

| | | | |
|---|---|---|---|
| 4,301,414 A | 11/1981 | Hill et al. | |
| 4,303,887 A | 12/1981 | Hill et al. | |
| 4,829,837 A * | 5/1989 | Telfer | 73/863.01 |
| 4,995,402 A | 2/1991 | Smith et al. | |
| 5,012,683 A * | 5/1991 | Davis | 73/864.24 |
| 5,039,617 A | 8/1991 | McDonald et al. | |
| 5,112,455 A | 5/1992 | Cozzette et al. | |
| 5,197,017 A | 3/1993 | Carroll et al. | |
| 5,200,051 A | 4/1993 | Cozzette et al. | |
| 5,423,206 A * | 6/1995 | Hetzel | 73/61.77 |
| 5,447,440 A | 9/1995 | Davis et al. | |
| 5,491,408 A | 2/1996 | Rousseau | |
| 5,502,651 A | 3/1996 | Jackson et al. | |
| 5,601,995 A | 2/1997 | Exner | |
| 5,628,961 A | 5/1997 | Davis et al. | |
| 5,686,562 A | 11/1997 | Toukatly et al. | |
| 6,673,622 B1 * | 1/2004 | Jina | 436/69 |

FOREIGN PATENT DOCUMENTS

WO     WO 96/00395     6/1995

\* cited by examiner

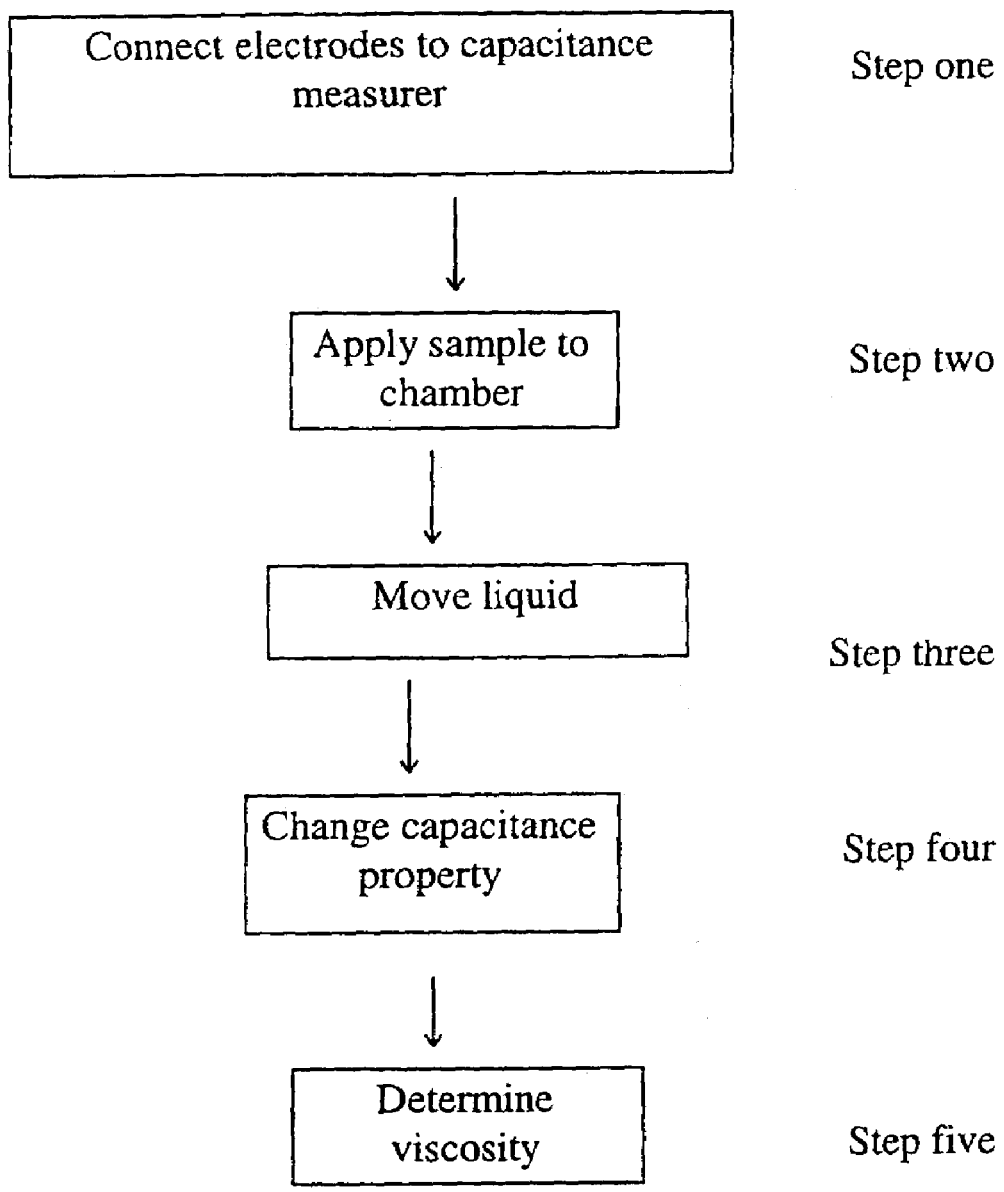

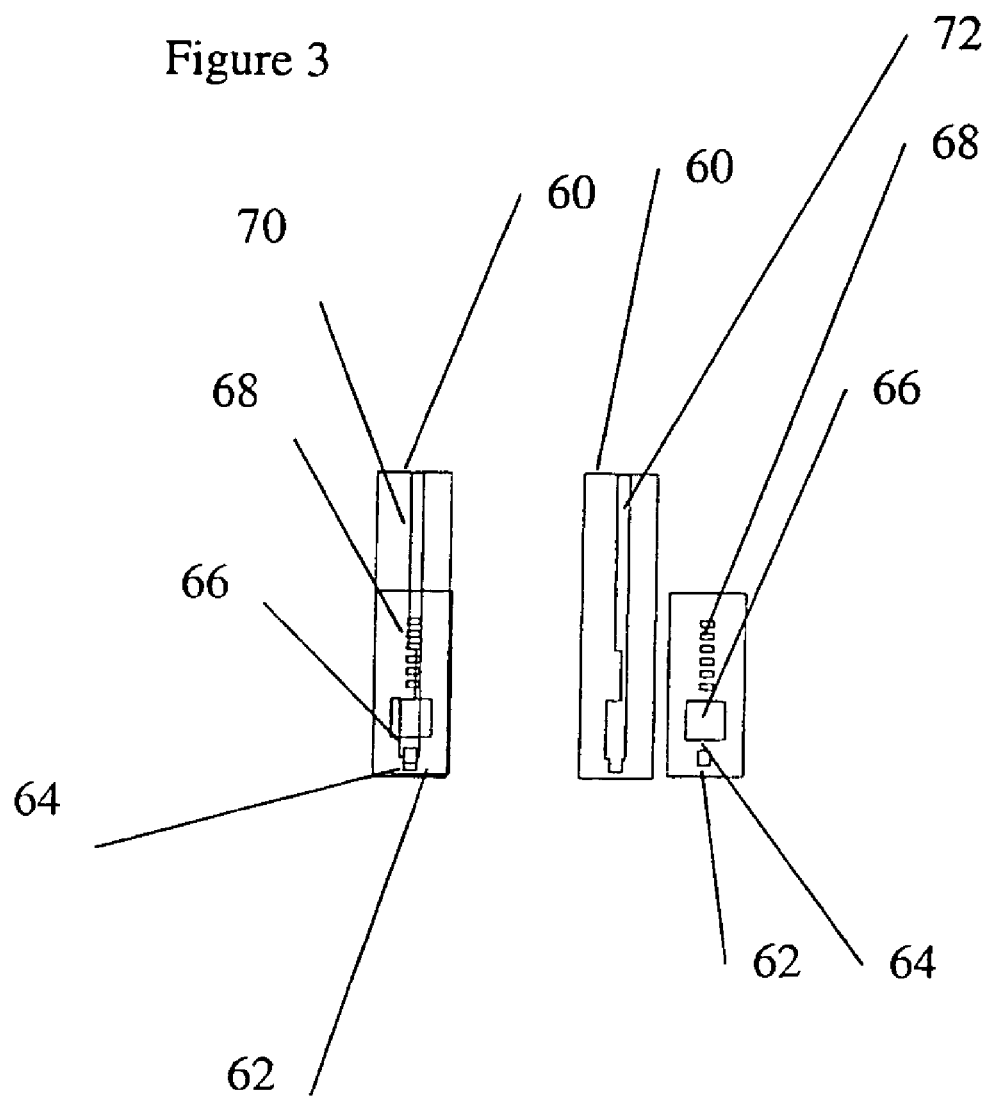

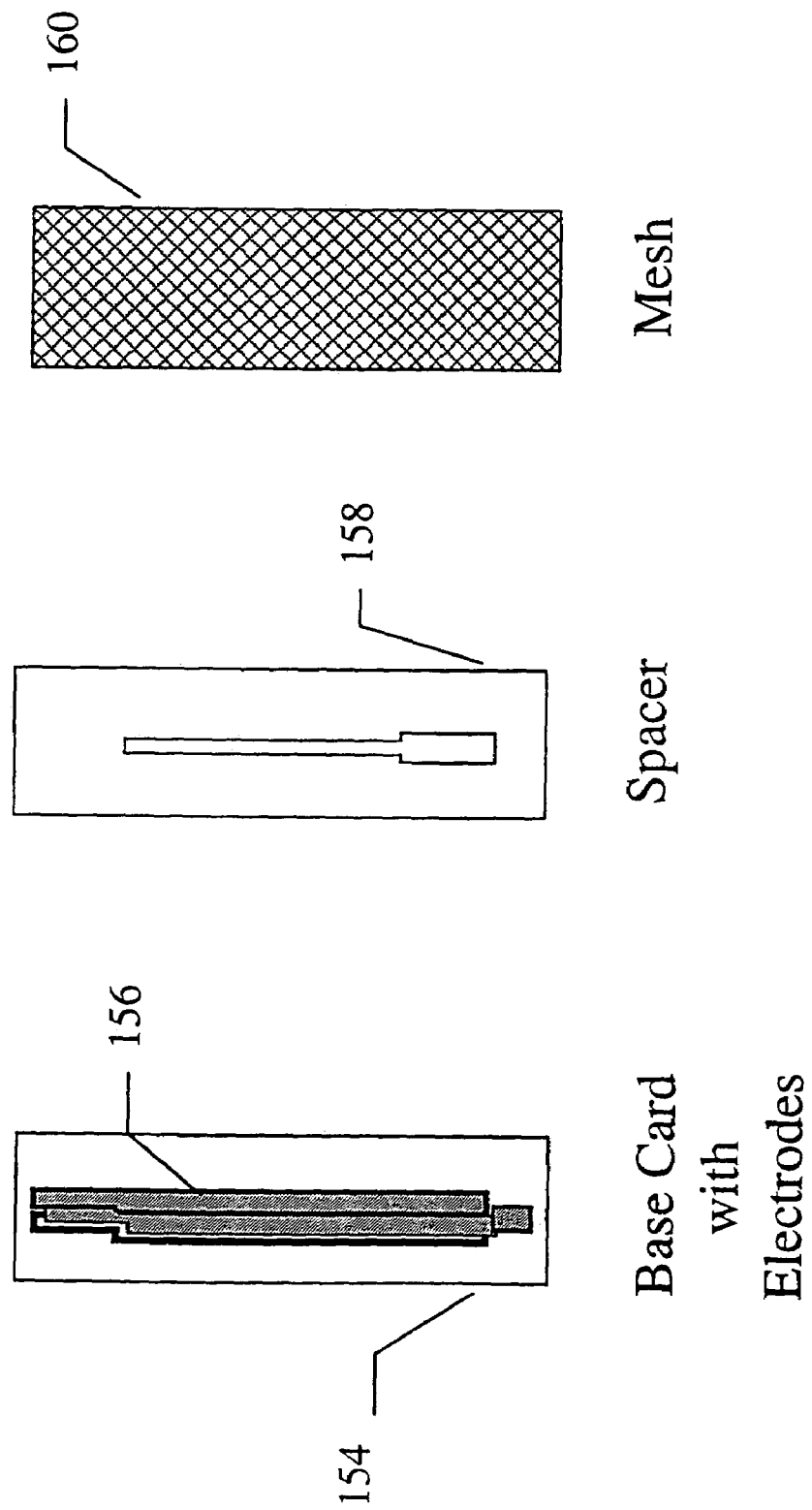

DEVICE FOR THE DETERMINATION OF BLOOD CLOTTING BY CAPACITANCE OR RESISTANCE

FIELD AND BACKGROUND OF THE INVENTION

The present invention relates to a device and method for determining viscosity of a liquid sample by capacitance or resistance, and, in particular, to a device and method for analyzing clotting of a blood specimen by a patient in a home testing environment, substantially without the need for intervention by highly trained clinical laboratory technicians or other technical medical personnel.

Clotting time is the amount of time required for a blood sample from a patient to clot. The determination of clotting time is important for patients who are receiving anti-coagulant therapy, such as those patients taking the drug warfarin, for example. The dosing regimen for such drugs must be determined for each individual patient, and then adjusted according to the clotting time. A dosing regimen which does not increase clotting time in one patient might result in an excessively and dangerously prolonged clotting time in another patient. The determination of dosing regimen is further complicated by the pharmacological properties of some anti-coagulant drugs, such as warfarin, which may remain highly bound to proteins in the blood, so that the amount of bioavailable drug in the body may be difficult to adjust. Thus, clotting time must be carefully monitored for each patient.

Unfortunately, currently clotting time can only be measured in a clinical laboratory setting by a clinical laboratory technician. The devices employed for the measurement of clotting time in the laboratory require the time period for clotting to be determined by optical or mechanical analysis of the blood sample. For example, a commercially available mechanical diagnostic assay is available from Boehringer Mannheim Corp and is based on the automated analysis of the behavior of metal balls which are stirred inside the plasma specimen by a magnet. These balls are examined with automated machine vision techniques to determine when the balls no longer move under the influence of the magnetic force. Clotting is assumed to have occurred when such lack of movement within the sample is observed. According to other disclosed diagnostic assays in the prior art, the blood sample to be analyzed is placed in a capillary. When the sample no longer moves through the capillary, clotting has occurred. The determination of the cessation of movement through the capillary is done by optical analysis. Optical analysis may be performed manually through observation of the sample within the capillary by a trained laboratory technician, or automatically by determining changes in the optical density of the blood sample with a light source and a photodetector.

For example, an optical device for manual visual detection of clotting has been disclosed in U.S. Pat. No. 3,951,606. A similar, disposable device has been disclosed in PCT Application No. WO 96/00395. More automated devices, in which changes in optical density are measured by sending a beam of light through the sample and detecting the amount of light which passes through the sample by a photodetector, are disclosed in U.S. Pat. No. 5,039,617 and U.S. Pat. No. 5,197,017. All of these devices suffer from the drawback of being either complex to operate or complex to construct. For example, measurement of clotting time by visual inspection of a blood sample as it moves through a capillary requires intense concentration in order to accurately determine the moment when the sample stops moving. Such concentration may not be difficult for a trained laboratory technician, but places an excessive burden on the lay patient who wishes to measure clotting time in a home testing environment. Thus, although at least one disposable version of a device for determination of clotting time by visual analysis has been disclosed in PCT Application No. WO 96/00395, as yet no such device is available for the home testing market.

The alternative form for optical analysis, in which a beam of light is transmitted from a light source through the blood sample to a photodetector, suffers from the drawback of being too complex and expensive to manufacture as a home testing device. Such a device would also require careful maintenance and calibration on a regular basis, which also places an excessive burden on the lay patient for home testing. Thus, automated optical analysis is not suitable for the home testing environment.

Devices for the electrical determination of blood clotting have also been disclosed. For example, one such device determined clotting of a blood sample by measuring changes in the electrical impedance of the sample (A. Ur, *Nature*, 226:269–270, 1970 and U.S. Pat. No. 3,699,437). A similar device was also disclosed in U.S. Pat. No. 3,674,012. However, this device required complex, delicate and sensitive laboratory equipment to measure the impedance of the sample, which would not be suitable for home testing. Furthermore, although the device was first disclosed more than twenty years ago, no commercially available equivalent device has been produced for the laboratory or for the home testing environment, an indication of the technical difficulties inherent in the design, production and operation of such a device. Thus, the measurement of electrical impedance is not suitable for the determination of clotting time in the home testing environment.

Other devices employing some type of electrical measurement of clotting time have been disclosed, but again none of these devices is suitable for the home testing environment. For example, U.S. Pat. No. 5,491,408 discloses a device which determines changes in viscosity of a liquid sample by measuring variations in voltage as the sample is agitated by a vibration generator. Clearly, such a device would be sensitive to vibrations in the environment and would therefore not be suitable for operation by a lay patient.

DDR (former East German) Patent No. DD 237454 discloses an apparatus for determining blood coagulation time. One electrode is dipped at intervals into a blood sample held in a metal block thermostat and then raised, and the capacitance between the raised electrode and the metal block is measured. As the blood coagulates, a filament of viscous liquid is attached to the raised electrode, changing the capacitance. This apparatus would certainly not be suitable for operation by a lay patient, since it requires careful manipulation of the equipment and manual monitoring of the progress of coagulation. Furthermore, the disclosed apparatus could not easily be automated in a small portable device. Thus, the apparatus disclosed in DDR Patent No. DD 237454 would certainly not be suitable for the home testing environment.

As another example, U.S. Pat. No. 5,601,995 discloses a device for detecting blood clotting. This device includes a porous sheet for receiving the blood sample. Clotting is then detected either optically or electrically, by the measurement of resistance. However, the porous sheet has a number of drawbacks as a receptacle for the blood sample. For example, various substances such as gelatin coating, surfactants or hydrophilic polymers are added to the sheet in order to overcome such problems as controlling the speed of transport through the porous medium and/or to promote adhesion of the fibrin clots (column 5, lines 16–34). In addition, since the blood (or any liquid specimen) moves inside the porous sheet, contact of the liquid with the electrodes, which touch the surface of the sheet, may not be sufficiently intimate to provide an accurate measurement of the electrical properties of the liquid specimen. Thus, the device disclosed in U.S. Pat. No. 5,601,995 is clearly deficient.

As yet another example, both U.S. Pat. No. 3,840,806 and PCT Application No. WO 94/16095 disclose devices which both measure electrical resistance and optical density of a sample. As noted previously, the measurement of optical density requires excessively complex equipment for the home testing environment. Furthermore, although over twenty years have passed since U.S. Pat. No. 3,840,806 was publicly disclosed, and four years have passed since PCT Application No. WO 94/16095 was publicly disclosed, no such device has been made available for the home testing environment, nor has any announcement been made of any clinical trials for such a device. Thus, clearly these prior art electrical devices have not proven to be suitable for operation by the lay patient.

One example of a device which has been successfully used by the lay patient in the home testing environment can be found in an entirely different medical area. Diabetics now use a small, highly portable electrical device for the determination of blood glucose levels. The operation of this device is quite simple. A drop of blood is taken from the patient and placed on a small card which is inserted into the device. After a brief period of time, the concentration of glucose in the sample is displayed on a small screen. Thus, commercially available glucose testing devices are simple to operate by the lay patient and are sufficiently robust to withstand the rigors of the home testing environment, yet are sufficiently accurate to generate clinically significant results.

Clearly, an equivalent device for the determination of clotting time in the home environment by the lay patient would be highly useful and commercially successful. Home testing of clotting time offers a number of advantages, including greater clinical utility of measurement through daily assessments rather than by a weekly or bi-weekly measurement at a clinic, and greater convenience for the lay patient, enabling the patient to immediately seek medical attention in response to any sudden changes in the measured clotting time. Currently, patients must travel to a clinic, have a blood sample withdrawn by a healthcare professional, and then wait for the results. Such a complicated, inconvenient and time-consuming process can potentially result in reduced patient compliance. By contrast, testing in the home is potentially both more convenient and less expensive, and may also result in increased patient compliance. Unfortunately, such a home testing device for the measurement of clotting time is simply not available. Thus, lay patients cannot currently measure clotting time in the home, but must instead resort to the less desirable process of clinical testing.

There is therefore a need for, and it would be useful to have, a method and a device for the measurement of clotting time which can be performed by the lay patient in the home testing environment, which would be both robust and accurate, which would also be simple to operate and which could potentially be employed to determine the viscosity of other types of liquid samples, preferably through the measurement of electrical capacitance, and which is substantially automated for relatively minimal intervention by a lay patient.

SUMMARY OF THE INVENTION

It is one object of the present invention to provide a novel device and method for the determination of the viscosity of any liquid, and in particular for the detection of changes in such viscosity.

It is another object of the present invention to provide a novel device and method for the determination of the clotting time of a blood sample.

It is yet another object of the present invention to provide such a device in which the blood sample undergoes an electrical analysis based upon the movement of the sample through a capillary channel, such that the distance traveled by the sample through the channel is proportional to the clotting time.

It is still another object of the present invention to provide such a device in which the electrical analysis is performed by measuring the electrical capacitance of the channel, by placing 2 flat electrodes on each side of the channel, or on top and below the channel, such that the amount of electrical capacitance between the electrodes is proportional to the distance traveled by the sample.

It is yet another object of the present invention to provide such a device in which the electrical analysis is performed, additionally or alternatively, by measuring current passing between two electrodes, one on either side of the channel, such that the amount of current is proportional to the distance traveled by the sample.

It is still another object of the present invention to provide such a device in which the electrodes are not in contact with the tested sample.

It is also another object of the present invention to provide the device for the determination of clotting time in a format which is suitable for operation by a lay patient in the home testing environment.

These and other objects of the present invention will become apparent from the figures, description and claims.

According to the present invention, there is provided a device for measuring a viscosity of a sample of a liquid, the device comprising: (a) a test chamber for receiving a test portion of the sample of the liquid, the test chamber featuring walls for defining an interior space of the test chamber; (b) a pair of electrodes disposed on the walls of the test chamber; and (c) a capacitance measuring circuit for measuring a capacitance of the test portion of the sample within the test chamber.

Preferably, the device further comprises: (d) an insulator for insulating the pair of electrodes such that the pair of electrodes are prevented from being in contact with the sample of liquid.

More preferably, the insulator includes the walls of the test chamber, such that the pair of electrodes is disposed externally to the walls.

Preferably, the capacitance measuring circuit further comprises: a capacitance measurer for determining a capacitance between the electrodes, such that the capacitance directly reflects a volume occupied by the test portion of the sample of the liquid.

Preferably, a lower surface of the test chamber has a shape selected from the group consisting of rectangular, square, circular and elliptical.

Also preferably, the device further comprises: (e) a receiver for causing the test chamber to receive the test portion of the sample of the liquid, the receiver being selected from the group consisting of a pump for pumping the test portion into the test chamber and a suction device for creating a vacuum.

Preferably, the test portion of the sample of the liquid enters the test chamber from a force selected from the group consisting of gravity, mechanical pressure and osmotic pressure.

Alternatively and preferably, the test portion of the sample of the liquid enters the test chamber from a capillary force induced by a capillary structure of the test chamber.

Preferably, the capillary structure is selected from the group consisting of a capillary depth of the test chamber, and a narrow channel shape of the test chamber.

Preferably, the sample of the liquid is selected from the group consisting of whole blood, plasma and serum. More preferably, the sample of the liquid is whole blood. Most preferably, a change in the viscosity of the whole blood is caused by coagulation, such that a volume of the test chamber being occupied by the test portion of the whole blood is determined according to the coagulation. Even more preferably, the test chamber features at least one coagulant agent being in contact with the test portion of the whole blood, the at least one coagulant agent altering a clotting property of the test portion of the whole blood. Also most preferably, the coagulant agent is an anti-coagulant, such that the test portion of the whole blood clots slower than the reference portion of the whole blood. Alternatively and most preferably, the coagulant agent is a pro-coagulating factor, such that the test portion of the whole blood clots faster than the reference portion of the whole blood.

Preferably, the at least one coagulant agent is dried onto the test chamber. Alternatively and preferably, the at least one coagulant agent is a liquid droplet placed onto the test chamber.

Preferably, the device further includes: (f) a clock for measuring a predetermined time period after the test chamber receives the whole blood, such that the amount of the capacitance is determined after the predetermined time period has elapsed. More preferably, the clock automatically begins measuring the predetermined time period after the test chamber receives the whole blood.

According to preferred embodiments, the device further comprises: (g) a disposable sensor, wherein the test chamber and the electrodes are located on the sensor, such that the whole blood is placed on one end of the disposable sensor; and (h) a sensor receptacle for receiving an opposing end of the disposable sensor such that the electrodes are in electrical contact with the capacitance measuring circuit. Preferably, the disposable sensor is a plastic card. More preferably, the test chamber, the power source, the measurer and the disposable sensor are characterized by being suitable for self-operation by a lay person.

According to other preferred embodiments, the device further comprises: (i) a reference chamber for drawing a reference portion of the whole blood from the one end of the disposable sensor; (j) at least one coagulant agent being in contact with the reference portion of the whole blood, the at least one coagulant agent altering a clotting property of the reference portion of the whole blood; (k) a second pair of electrodes disposed on the reference chamber, the second pair of electrodes being in substantially direct electrical contact with the sensor receptacle, such that when the reference portion of the whole blood is drawn into the reference chamber, a second amount of capacitance is measured by the measurer, such that the second amount of capacitance is a reference capacitance; and (l) an analyzer for determining a clotting time of the whole blood by comparing the reference capacitance to the measured capacitance. Preferably, the first and second pairs of electrodes share a common electrode. More preferably, the coagulant agent is an anti-coagulant, such that the reference portion of the whole blood clots slower than the test portion of the whole blood.

Alternatively and preferably, the coagulant agent is a pro-coagulating factor, such that the reference portion of the whole blood clots faster than the test portion of the whole blood. Preferably, the at least one coagulant agent is dried onto the disposable sensor. Alternatively and preferably, the at least one coagulant agent is a liquid droplet placed onto the disposable sensor.

Preferably, the clotting time is determined as a prothrombin time. Alternatively and preferably, the clotting time is determined as a partial prothrombin time.

Preferably, the electrodes are constructed from a material selected from the group consisting of carbon, graphite and metal. More preferably, the material is a carbon, graphite or metal impregnated film. Alternatively and more preferably, the metal is in a form selected from the group consisting of film, foil, metal impregnated film and metal sputtered film. Most preferably, the metal is selected from the group consisting of silver, aluminum, titanium, stainless steel, palladium, copper and a mixture of silver and silver chloride.

According to yet other preferred embodiments, the electrodes extend along substantially the entirety of the test chamber. Preferably, the electrodes are disposed on opposing sides of the test chamber. More preferably, the electrodes extend along a portion of the test chamber, a length of the portion being shorter than a length of the test chamber.

Most preferably, the electrodes are disposed on opposing sides of the test chamber and a first electrode of the electrodes is on a side nearer an entrance of the test chamber than a second electrode of the electrodes, such that the viscosity of the sample of liquid is determined by a period of time required for the sample to travel from the first electrode to the second electrode, such that a capacitance is measurable substantially only when the sample occupies substantially all the area located between both the first electrode and the second electrode.

According to still other preferred embodiments, the chamber features a plurality of surfaces, and the plurality of surfaces is pretreated. Preferably, the pretreated surfaces are pretreated by being soaked in a buffer containing an ingredient selected from the group consisting of a detergent and a hydrophilic polymer.

According to yet other preferred embodiments, the device further features a cover for covering said test chamber, said cover featuring at least one aperture. More preferably, the cover features a plurality of apertures arranged as a mesh.

According to another embodiment of the present invention, there is provided a kit for measuring a clotting time of a sample of blood from a patient, comprising: (a) a disposable sensor for receiving the blood sample at an end of the sensor, the sensor including: a test chamber for drawing a test portion of the blood sample from the end of the sensor, the test chamber featuring walls for defining an interior space of the test chamber; (b) a pair of electrodes disposed in contact with the walls of the test chamber; (c) a capacitance measuring circuit for measuring the first capacitance, such that the first capacitance is a measured capacitance, the capacitance measuring circuit being in electrical contact with at least one of the pair of electrodes; and (d) an analyzer for determining the clotting time according to the measured capacitance.

Preferably, the pair of electrodes is integrally formed with the capacitance measuring circuit. Alternatively and preferably, the pair of electrodes is integrally formed with the test chamber.

Preferably, the kit further comprises: (e) a needle for breaking a skin of the patient for obtaining the blood sample.

According to still another embodiment of the present invention, there is provided a method for determining a viscosity of a sample of a liquid, the method comprising the steps of: (a) providing a capacitance measuring circuit and a test chamber with a plurality of walls, the test chamber featuring two electrodes, the electrodes being located externally on the walls of the test chamber; (b) contacting the electrodes to capacitance measuring circuit; (c) placing the sample of the liquid in the test chamber, such that the sample is able to contact both electrodes; (d) allowing the sample to spread through the test chamber; and (e) determining a capacitance between the electrodes, the capacitance directly reflecting a volume of the test chamber occupied by the sample of the liquid.

Preferably, the method further comprises the steps of: (f) providing a reference chamber, the reference chamber featuring two electrodes; (g) connecting the capacitance measuring circuit to the reference electrodes; (h) placing a reference portion of the whole blood in the reference chamber; (i) allowing the reference portion to spread through the reference chamber; (j) measuring a reference capacitance between the reference electrodes, and (k) determining the clotting time according to a comparison between the reference capacitance and the measured capacitance.

According to still another embodiment of the present invention, there is provided a method for determining a viscosity of a sample of a liquid, the method comprising the steps of: (a) providing a capacitance measuring circuit and a test chamber, the test chamber featuring two electrodes, each of the electrodes being shorter than a length of the test chamber, a first of the electrodes being located closer to an entrance of the test chamber than a second of the electrodes; (b) connecting the capacitance measuring circuit to the electrodes; (c) placing the sample of the liquid in the test chamber, such that the sample is located near the first electrode; (d) allowing the sample to spread within the test chamber; and (e) determining a period of time required for the sample to be in proximity to the second electrode, the period of time directly reflecting an amount of the surface of the electrodes being in proximity to the sample of the liquid.

According to yet another embodiment of the present invention, there is provided a device for measuring a viscosity of a sample of an electrically conductive liquid, the device comprising: (a) a test chamber for receiving a test portion of the sample of the electrically conductive liquid; (b) two electrodes disposed in the test chamber such that the test portion of the sample of the electrically conductive liquid is able to contact both of the electrodes; (c) a power source for supplying electrical power to the electrodes; and (d) a measurer for determining a resistance between the electrodes, such that the resistance directly reflects an amount of a surface area of the electrodes being contacted by the test portion of the sample of the electrically conductive liquid.

According to still another embodiment of the present invention, there is provided a kit for measuring a prothrombin time of a blood sample of blood from a patient, comprising: (a) a disposable sensor for receiving the blood sample at an end of the sensor, the sensor including: (i) a test chamber for drawing a test portion of the blood sample from the end of the sensor; and (ii) a pair of electrodes disposed on the test chamber, such that the sample of blood is able to contact the pair of electrodes; (b) a voltage generator for generating a voltage, the voltage generator being in electrical contact with the pair of electrodes such that when the test portion of the blood sample is drawn into the test chamber, a first electrical current is passed between the pair of electrodes; (c) a measurer for measuring the first electrical current, such that the first electrical current is a measured current; and (d) an analyzer for determining the clotting time according to the measured current.

According to yet another embodiment of the present invention, there is provided a method for determining a viscosity of a sample of an electrically conductive liquid, the method comprising the steps of: (a) providing a test chamber, the test chamber featuring two electrodes; (b) supplying electrical power to the electrodes; (c) placing the sample of the liquid in the test chamber, such that the sample is able to contact both electrodes; (d) allowing the sample to spread over a surface of both electrodes; and (e) determining a resistance between the electrodes, the resistance directly reflecting an amount of the surface of the electrodes being contacted by the sample of the liquid.

Preferably, the resistance is determined indirectly by measuring an amount of a current passing between the electrodes, such that the current is a measured current. More preferably, the clotting time is measured by determining the amount of the current after a predetermined period of time has elapsed. Alternatively and more preferably, the clotting time is measured by determining a period of time required for the amount of the current to reach a predetermined level.

According to still another embodiment of the present invention, there is provided a device for detecting an interaction of a first acceptor and a second acceptor through a determination of a change of a viscosity of a sample of an electrically conductive liquid, the sample containing the second acceptor, the viscosity of the liquid changing upon the interaction of the first and second acceptors, the device comprising: (a) a test chamber for receiving a test portion of the sample of the electrically conductive liquid, the test chamber featuring the first acceptor; (b) two electrodes disposed in the test chamber such that the test portion of the sample of the electrically conductive liquid is able to contact both of the electrodes; (c) a power source for supplying electrical power to the electrodes; and (d) a measurer for determining a current flowing between the electrodes, such that the current directly reflects an amount of a surface area of the electrodes being contacted by the test portion of the sample of the electrically conductive liquid, and such that the current is proportional to the change in the viscosity of the liquid. Preferably, the liquid is whole blood, and the first acceptor features a coagulation agent, such that the change in the viscosity of the liquid is caused by coagulation substantially only if the first and second acceptors interact. Alternatively and preferably, the liquid is a solution of DNA, and the first acceptor features a DNAase, such that the change in the viscosity of the liquid is caused by cleavage of DNA substantially only if the first and second acceptors interact.

Hereinafter, the term "subject" refers to the human or lower mammal upon which the method and system of the present invention are performed or operated. Hereinafter, the term "patient" refers to any human from which a blood sample may be drawn for analysis by the device and method of the present invention. Hereinafter, the terms "self-testing" and "self-operating" refer to the analysis of a blood sample from a patient either by the same patient or by another lay individual who is not a medical professional. Hereinafter, the terms "home testing environment" and "home environment" refer to an environment other than a clinic, clinical or research laboratory, office of a medical professional or hospital. An example of a home testing environment would be the home of a patient.

Hereinafter, the term "clotting time" includes the measurement of any parameter related to the time period required for a blood sample to clot. Examples of these parameters include, but are not limited, prothrombin time and partial prothrombin time. Hereinafter, the term "blood sample" may include, but is not limited to, a sample of whole blood, plasma or serum.

Hereinafter, the term "electrode" refers to any conductor which is capable of conducting electricity and is suitable for the measurement of electrical capacitance.

BRIEF DESCRIPTION OF THE DRAWINGS

The foregoing and other objects, aspects and advantages will be better understood from the following detailed description of a preferred embodiment of the invention with reference to the drawings, wherein:

FIG. 1 shows a flow chart of an exemplary method according to the present invention;

FIG. 3 is a schematic block diagram of another embodiment of the device of the present invention, which features apertures in the cover of the chambers of the sensor;

FIGS. 6A–6C show the effect of the addition of coagulant to blood samples on the measurement of current by a device of the present invention, in which FIG. 6A shows the time to the maximum current, FIG. 6B is the measured current after a fixed time period has elapsed and FIG. 6C shows the corrected measured current;

FIG. 8 shows yet another embodiment of the device of the present invention, which features a mesh for the cover of the chambers of the sensor;

DETAILED DESCRIPTION OF PREFERRED EMBODIMENTS

Figure 2A:
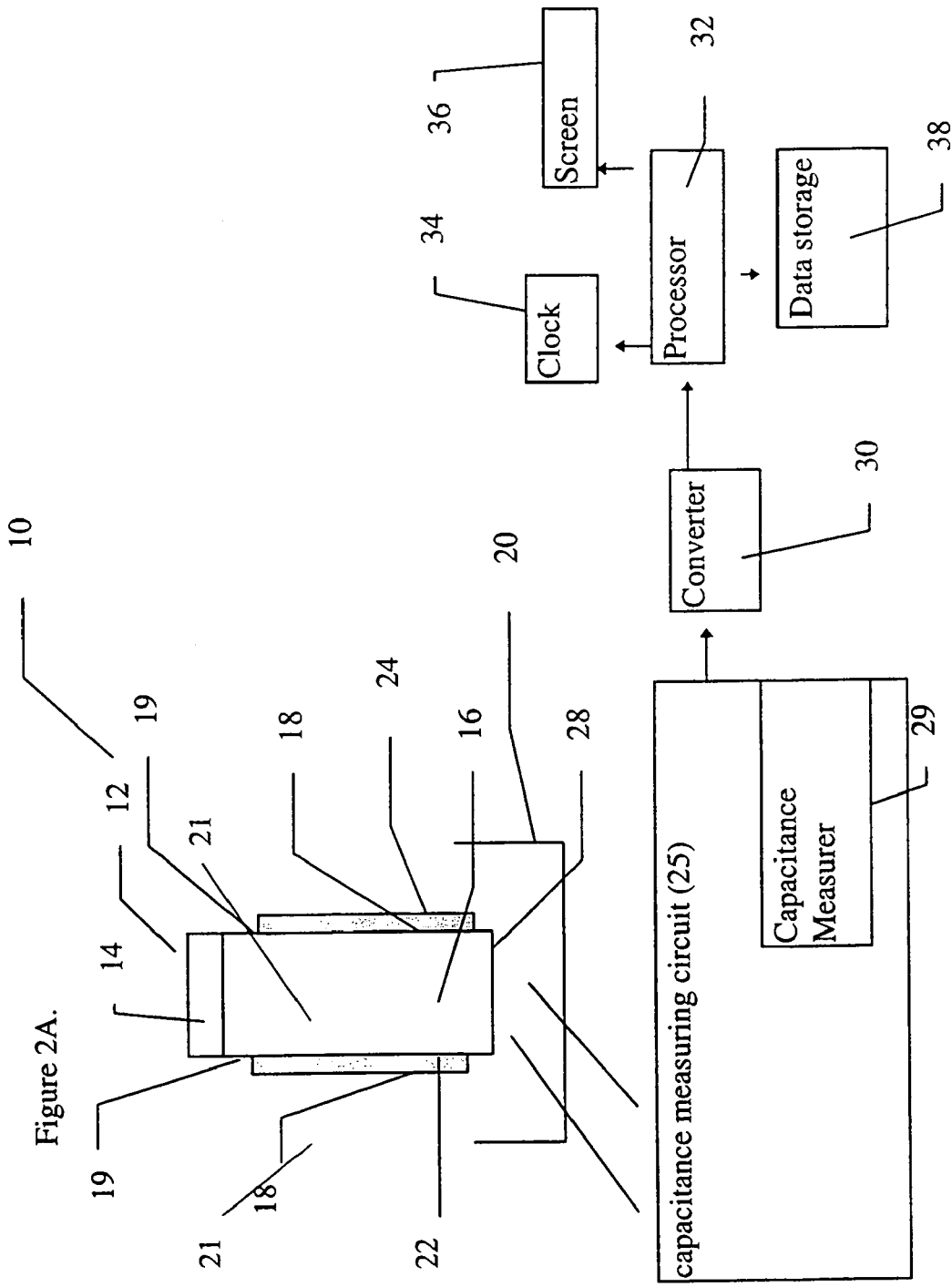
FIGS. 2A–2D are schematic block diagrams of various embodiments of exemplary devices for the determination of clotting time according to the present invention.

The present invention is directed to a method and a device for the determination of the viscosity of a liquid sample, and in particular for the measurement of the clotting time of a blood sample, especially in the home testing environment. The device of the present invention includes a body which is intended to receive a disposable card, or other disposable sensor, on which a blood sample is placed. The sensor is inserted into the body of the device, which then measures an electrical property, such as the capacitance of the sample. The measured capacitance is then used to determine clotting time. Alternatively, an electrical property such as the amplitude of current passed through the sample is used to determine clotting time. Preferably, the determined clotting time is then displayed on a screen, for example.

The electrical property could be determined by placing two electrodes on either side of a test chamber. In a preferred embodiment, the electrodes do not contact the liquid sample, but are isolated from it by either placing the electrodes on the outside walls of the chamber, or by coating the electrodes with an electrically insulating material. The distance traveled by the liquid sample through the chamber, such as a blood sample before clotting, would be directly related to the viscosity of the liquid. For example, the time period required for the maximum capacitance to be reached could be measured. Alternatively, the capacitance could be measured after a fixed time period had elapsed. Also alternatively, the time period required for the maximum current to be reached could be measured, or the amount of current could be measured after a fixed time period had elapsed.

According to one preferred embodiment of the present invention, the electrodes could be arranged such that both electrodes extended the length of the chamber, for example along the outer walls, or otherwise insulated from the liquid sample, for example by an additional insulating layer. Alternatively and preferably, both electrodes would be relatively short so as to extend only along a portion of the chamber. One electrode would be placed substantially closer to the start of the chamber than the other, without any overlap. The time required for capacitance to be measurable or alternatively to reach a certain level would determined in order to calculate the viscosity of the liquid or the clotting time, for example. Alternatively, the time required to close the circuit would be optionally determined in order to calculate the viscosity of the liquid or the clotting time, as another example.

According to another preferred embodiment of the present invention, the device further includes a reference chamber for the determination of clotting in a control sample.

The principles and operation of a method and a device for the determination of clotting time according to the present invention may be better understood with reference to the drawings and the accompanying description, it being understood that these drawings are given for illustrative purposes only and are not meant to be limiting.

The following description is divided into three sections. The first section describes the measurement of capacitance in a liquid sample, such as a blood sample. The second section describes the measurement of resistance in the liquid sample. The third section describes the detection of the interaction of a ligand/receptor pair with the device of the present invention.

Section 1: Measurement of Capacitance

Referring now to the drawings, FIG. 1 shows a flow chart of an exemplary method for determining the viscosity of a liquid according to the present invention. In step one, power is supplied to the electrodes. For example, a constant voltage could be applied across the electrodes. The electrodes are preferably flat, and are insulated from the liquid, such that the liquid does not directly contact the electrodes. The power being supplied should be alternating voltage.

In step two, a sample of the liquid is placed at the entrance to a chamber with two electrodes. The lower surface of the chamber could be any suitable shape including, but not limited to, a square, a rectangle, a circle and an ellipse. The chamber preferably features only a single capillary channel.

In step three, the liquid moves through the chamber through the action of a receiver, for example by capillary action, or by application of a vacuum, by gravity, or through mechanical or osmotic pressure, thereby increasing the surface area of the electrodes which is covered by the liquid, although the liquid does not directly contact any portion of the electrodes. Instead, the liquid spreads within the chamber, such that the volume of the liquid within the chamber is directly correlated to the measured capacitance. The vacuum could be applied by the presence of a suction device which is an example of the receiver. The capillary action could be caused by a capillary structure such as a capillary depth of the chamber, and/or a narrow channel shape of the chamber. The capillary depth of the chamber would be a depth selected to ensure that the liquid would enter the chamber through the capillary action.

In step four, the movement of the liquid causes an electrical property to alter as the volume occupied by the liquid increases. For example, the measured capacitance could increase. For the measurement of capacitance, a capacitance meter should be electrically connected to the electrodes. In step five, the alteration of the electrical property is used to determine the viscosity of the liquid sample.

The method of the present invention could be used to measure the viscosity of a blood sample as it clots, for example. The blood sample would be taken from the patient and then placed at the entrance to the chamber, as described previously. The clotting time could then be determined by measuring the capacitance after a fixed time period had elapsed, or by measuring the period of time required to reach the maximum capacitance, for example. In either case, the length of time required for the blood sample to clot would be directly related to the volume occupied by the sample before clotting occurred. For example, if the capacitance was measured after a fixed time period had elapsed, the amount of the various measured amounts of capacitance would increase as the clotting time also increased, as this would permit the blood sample to travel farther down the chamber before clotting occurred. Similarly, if the time period required to reach the maximum capacitance was measured, this time period would increase as the clotting time also increased. Thus, as the clotting time increased, the volume of the chamber occupied by the sample before clotting occurred would also increase.

The advantage of measuring the capacitance, rather than the amount of current passing between the two electrodes for example, is that the measurement of capacitance does not alter the sample itself. Since the sample substantially never directly contacts any portion of the electrodes, the properties of the sample are not altered by the electrodes and/or by the voltage supplied to the electrodes. By contrast; in order to measure current passing through the sample, at least a portion of the electrodes must directly contact the sample. Such direct electrical contact consumes electrochemical species in the blood sample, which in turn decreases the amount of current passing through the sample. However, movement of the blood sample farther into the chamber increases the volume of the chamber occupied by the sample, and hence increases the amount of current passing through the sample. These two opposing trends may decrease the accuracy of the measurement of blood coagulation. Thus, the measurement of capacitance is clearly more accurate.

Although the description of exemplary devices for measuring the viscosity of a liquid sample according to the present invention is specifically drawn to devices for determining the clotting time of a blood sample, it is understood that this is for the sake of clarity only and is not meant to be limiting. As noted previously, the method and device of the present invention could also be used to determine the viscosity of substantially any type of liquid sample, as such viscosity is directly related to the volume of the chamber occupied by the sample as the liquid sample moves through the chamber.

FIGS. 2A–2D are schematic block diagrams of exemplary devices for the determination of clotting time by measuring capacitance according to the present invention. FIG. 2A shows a first embodiment of an exemplary device. A clotting diagnostic device 10 is shown with a sensor 12 inserted. Sensor 12 features a sample area 14 onto which a blood sample is placed (not shown). The blood sample is drawn into a test chamber 16 formed between two electrodes 18, for example by capillary action. Alternatively and preferably, device 10 could include a pumping for pumping the sample into test chamber 16, or a suction device for sucking the sample into test chamber 16, for example. The sample could also enter test chamber 16 through mechanical or osmotic pressure, or the application of a vacuum. Preferably, test chamber 16 is a single capillary channel as shown.

The sample is preferably not able to directly contact electrodes 18. Electrodes 18 are preferably either insulated with an insulating layer (not shown) or are alternatively and preferably placed externally to walls 19 of test chamber 16, both of which options are herein collectively described as an insulator 21.

In this embodiment, both test chamber 16 and electrodes 18 are formed on sensor 12. Alternatively and preferably, test chamber 16 and electrodes 18 could be formed within sensor receptacle 20 (not shown). Also alternatively and preferably, electrodes 18 could be formed within sensor receptacle 20, but test chamber 16 could be formed on sensor 12, as shown in FIG. 2D. Since sensor 12 is preferably disposable for easy cleaning and maintenance of device 10, the illustrated arrangement of either FIG. 2A, in which both test chamber 16 and electrodes 18 are formed on sensor 12, or of FIG. 2D, in which electrodes 18 are formed within sensor receptacle 20, and test chamber 16 is formed on sensor 12, is preferred. For any of these embodiments, electrodes 18 are positioned such that the sample does not directly contact electrodes 18, since electrodes 18 are insulated with insulator 21, for example by being insulated with an insulating layer or by being placed outside walls 19. Also for either embodiment, the blood sample is placed onto sensor 12 which is in contact with sensor receptacle 20.

Sensor receptacle 20 is in electrical contact with a capacitance measurement circuit 25. The design of capacitance measuring circuits, such as capacitance measuring circuit 25, is well known in the art of electronic circuit design. Capacitance measuring circuits are incorporated in many commercially available multi-meter instruments, such as those manufactured by Thurlby Thandar Instruments (TTi 1705; Huntingdon, Cambridgeshire, UK), Fluke Technology (USA), Keithley Instruments (USA), and Appa Technology (APPA 93 Multimeter; Taiwan), or in dedicated capacitance meters, such as those manufactured by TES (TES-1500; Taiwan). Also shown is a measuring device for measuring capacitance, shown as a capacitance measurer 29. As shown, capacitance measuring circuit 25 is attached to both electrodes 18, designated as a first electrode 22 and a second electrode 24, on sensor 12. Electrodes 18 are also shown disposed in parallel on opposing sides of test chamber 16, since for proper and sensitive capacitance measurement, at least one electrode 18 should preferably be on each side.

Methods and materials for manufacturing electrodes 18 and sensor 12 are well known in the art. The material could be in the form of a metal foil or film, or carbon or metal impregnated film or metal sputtered film, for example. Sensor 12 could be a card made from any type of suitable plastic, preferably semi-rigid or rigid plastic. Electrodes 18 could be screen printed onto sensor 12 according to methods well known in the art. Chamber 16 could be formed onto sensor 12 according to various microfabrication techniques which are well known in the art (see for example U.S. Pat. No. 5,120,420), such that electrodes 18 are insulated by an insulator 21.

For example, sensor 12 could be a plastic card formed from polyester or polycarbonate. Silver paste could then be screen printed onto sensor 12 to form electrodes 18. The assembly would then be dried. Insulating paste could optionally be screen printed onto sensor 12 such that both electrodes 18 are not exposed within chamber 16. The assembly would again be dried. Finally, a spacer and cover made from plastic film or foil could be attached to sensor 12 in order to form a chamber 16 which could be a capillary channel.

In the embodiment shown, the blood sample is placed onto sample area 14 and is then drawn into test chamber 16 by capillary action. The dimensions of test chamber 16 should therefore permit such capillary action to occur. Such dimensions could be easily selected by one of ordinary skill in the art. An opposing end 28 of sensor 12, opposing sample area 14, is then placed in contact with sensor receptacle 20, for example by inserting sensor 12 into sensor receptacle 20.

Alternatively and more preferably, opposing end 28 of sensor 12 is first placed in contact with sensor receptacle 20. Next, voltage, preferably alternating, is applied to electrodes 18 from capacitance measurement circuit 25. Finally, the blood sample is placed onto sample area 14 by the patient, for example by using a needle (not shown) to break the skin of the patient and to allow the blood sample to be collected. The term "needle" includes any sharp point or edge which can break the skin of the patient. In this embodiment, device 10 could be a kit for determining the clotting time of the blood sample from the patient in the home testing environment.

This particular mode of operation is more preferred because the application of the blood sample can automatically trigger the timing function. For example, when sensor 12 is placed in contact with sensor receptacle 20 before a blood sample has been applied, the measured capacitance would be low. As soon as the blood sample was applied, the measured capacitance would increase, enabling device 10 to automatically detect the presence of the blood sample.

As blood sample flows through test chamber 16, the liquid flows between the electrodes 18, one on either side of test chamber 16, causing an increase of, the electrical capacitance between first electrode 22 and second electrode 24.

After measuring the capacitance, meter 29 then converts the measured capacitance to a digital signal by a converter 30. The digital signal is then sent to a processor 32 for analysis of the signal and the calculation of the clotting time from the signal. Processor 32 includes instructions for calculating the clotting time from the signal. Processor 32 also includes a clock 34 for accurately measuring time. Such clocks suitable for micro-processors and other computational devices are well known in the art. Processor 32 could be a dedicated microprocessor with ROM (read-only memory) memory for storing the instructions, for example. Circuits which perform calculations for performing a diagnostic test according to the electrical property of a sample of blood already exist in portable electrochemical blood glucose meters, such as those distributed by Bayer, under the trade name of Glucometer Elite™, and by Medisense, under the trade name Exactech™.

Preferably, the calculated clotting time is displayed on a display screen 36. Also preferably, the clotting time, and any other desired information, is stored in a data storage area 38, which could be a flash memory array for example.

The clotting time could be calculated in a variety of ways. For example, the blood sample could be allowed to flow through test chamber 16 until clotting had occurred, at which point blood sample would cease to flow. The cessation of blood flow through test chamber 16 could be determined by noting the time point at which the amount of capacitance reaches a maximal value. The clotting time would then be determined according to this time point. Alternatively and preferably, the amount of capacitance could be measured at a fixed time point, after a predetermined period of time had elapsed from the time at which sensor 12 was placed in contact with sensor receptacle 20.

Figure 2B:
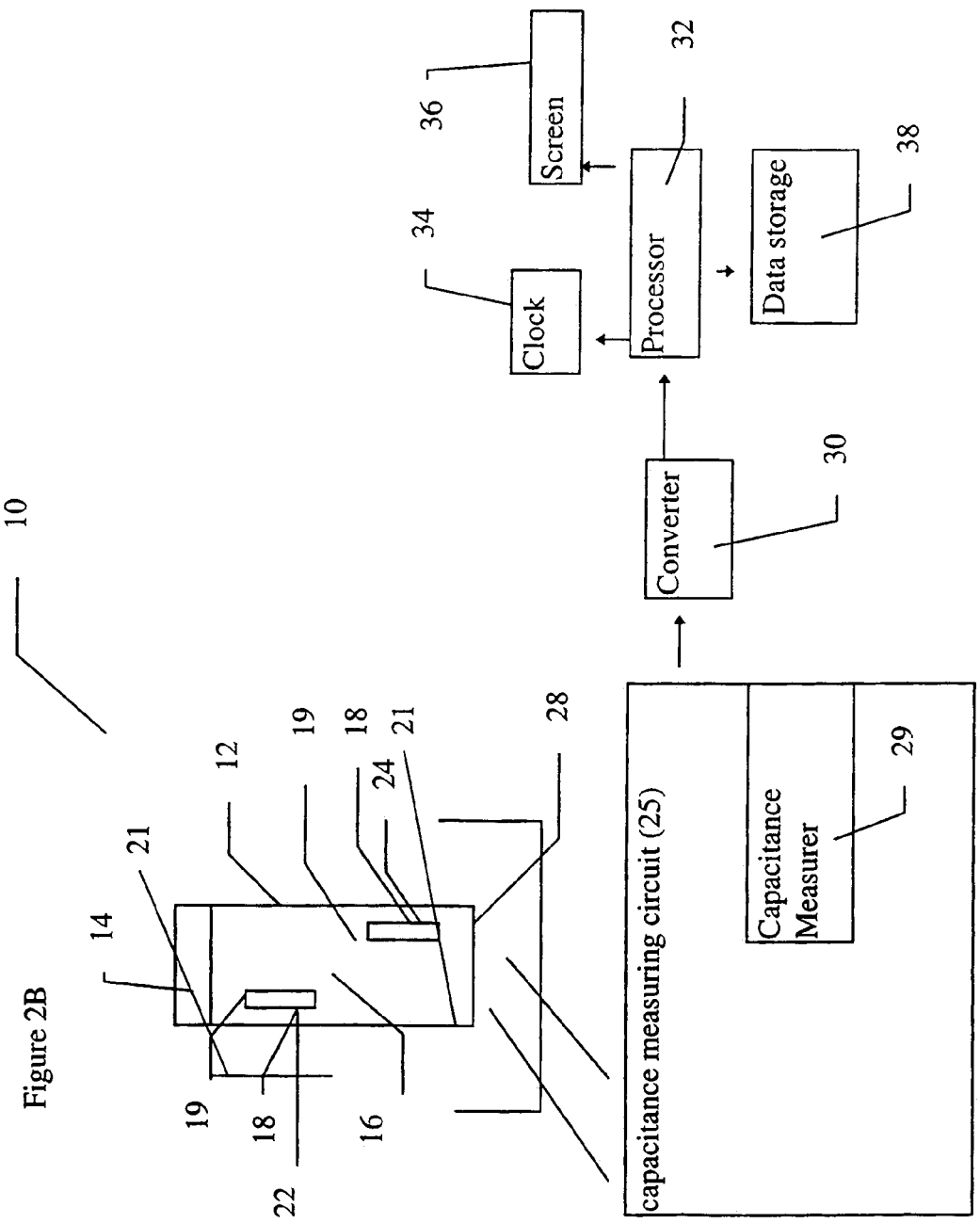

According to yet another preferred embodiment of the device of the present invention, shown in FIG. 2B, electrodes 18 could be arranged such that neither electrode 18 extends along substantially a majority of, or substantially the entirety of, the length of test chamber 16. Instead, preferably, both electrodes 18 are relatively short so as to extend only along a portion of walls 19 of test chamber 16, this portion being substantially shorter than the majority of the length of test chamber 16. First electrode 22 would be placed substantially near the start of test chamber 16, close to sample area 14. Second electrode 24 would then be placed farther along test chamber 16, substantially closer to opposing end 28 of sensor 12. Of course, the positions of first electrode 22 and second electrode 24 could also be reversed (not shown). In any case, first electrode 22 and second electrode 24 should not be placed such that there is any overlap between first electrode 22 and second electrode 24. As for FIG. 2A, electrodes 18 are also shown disposed in parallel on opposing sides of test chamber 16. Again, optionally and preferably, both electrodes 18 could be placed on one side of walls 19 of test chamber 16 in series, one after the other (not shown).

In this preferred embodiment, the time required to substantially increase the capacitance is determined in order to calculate the clotting times rather than measuring the amount of capacitance. The time required to increase the capacitance to a predetermined level is the period of time required for the blood sample to proceed from first electrode 22, which is closer to sample area 14, to second electrode 24, such that the blood sample is in close proximity both to first electrode 22 and to second electrode 24. Alternatively and preferably, the amount of time during which the capacitance increases could also be measured, such that the time would be measured until the capacitance reaches a plateau and stops increasing. These embodiments have an advantage since the actual value of the capacitance is not important for the measurement of the clotting time, but only relative changes in the capacitance.

Figure 2C:
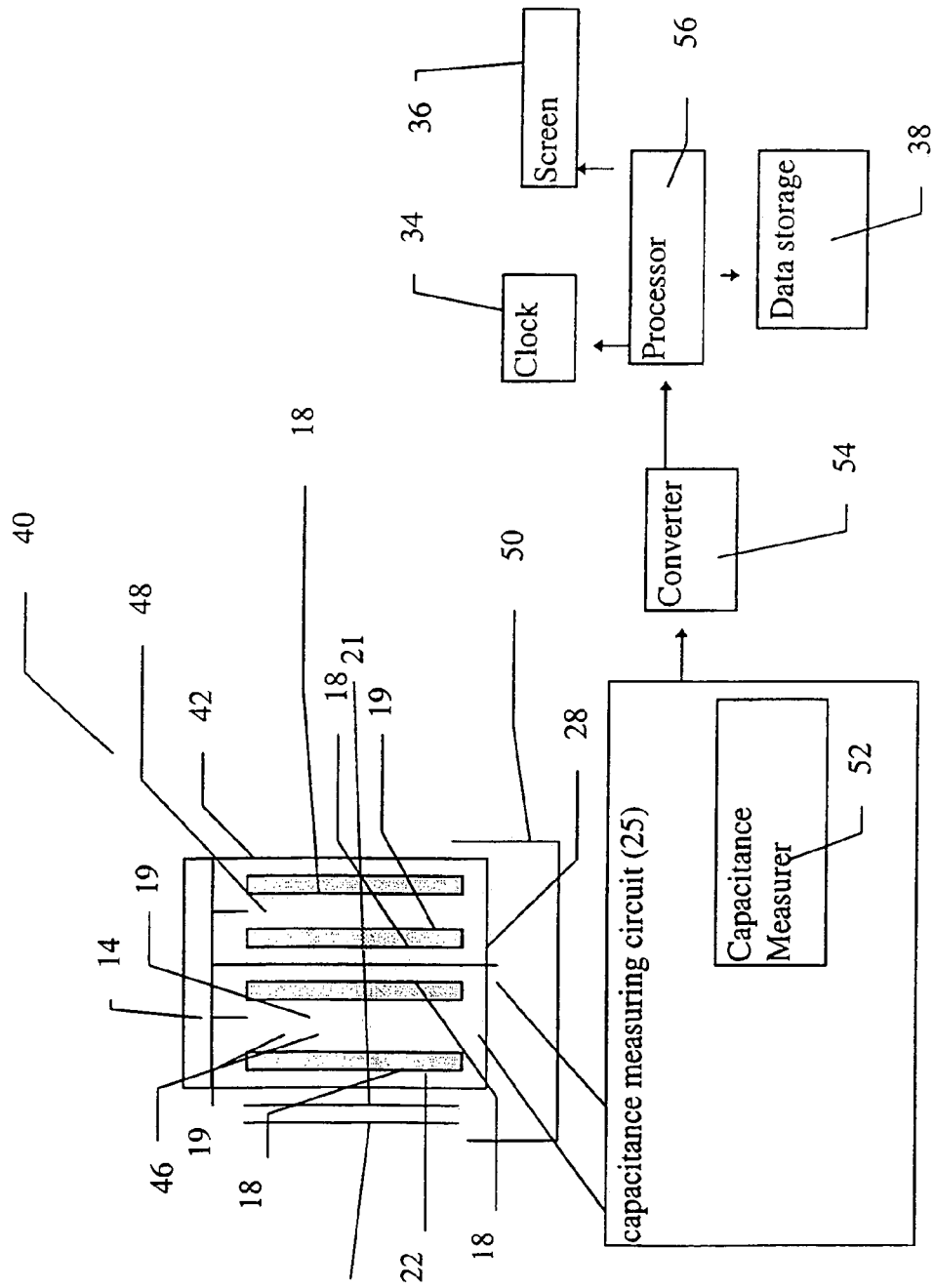
Figure 2D:
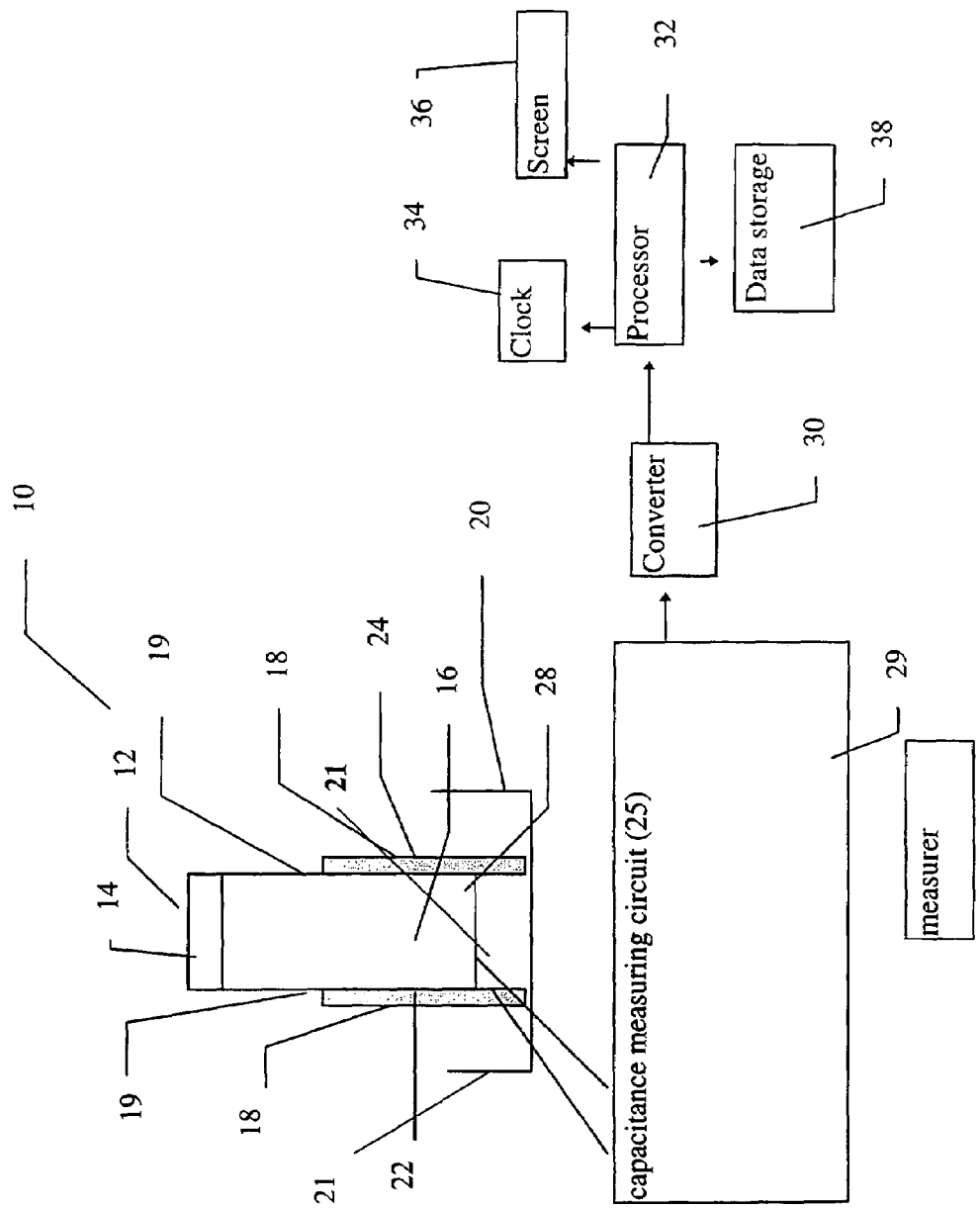

FIG. 2C is a block diagram of a third exemplary embodiment, in which the device of the present invention is able to compare the clotting time of the blood sample with the behavior of a control sample. In this embodiment, a clotting diagnostic device 40 also features a sensor 42. Sensor 42 also has sample area 14. Blood is placed on sample area 14 and then flows into two chambers 44, a test chamber 46 and a reference chamber 48. Preferably, the blood sample is divided equally, such that a substantially equal portion of the sample flows into each channel 44. Both test chamber 46 and reference chamber 48 each feature two electrodes 18, as described previously. Preferably, both chambers 46 and 48 can share one reference or ground electrode (the center one), thereby simplifying electrical circuits and saving space on the sensor. Although electrodes 18 are shown arranged as for the first embodiment of FIG. 2A, electrodes 18 could also be arranged according to the second embodiment shown in FIG. 2B. As for both FIGS. 2A and 2B, electrodes 18 are also shown disposed in parallel on opposing sides of test chamber 46 or of reference chamber 48. Again, both electrodes 18 could be placed on one side of test chamber 46 or of reference chamber 48 (not shown). The surface of electrodes 18 is preferably insulated by an insulator 21, for example by being placed outside wall or walls 19, or by being insulated with an insulating layer (not shown), and does not contact the tested liquid. Furthermore, test chamber 46 is functionally equivalent to chamber 16, as described for FIGS. 2A and 2B.

Reference chamber 48 preferably features at least one factor for altering the clotting behavior of the blood sample, present either as a liquid droplet for a wet reagent, or dried for a dry reagent. For example, reference chamber 48 could include a predetermined amount of an anti-coagulant factor, such that the clotting time of the portion of the blood sample in reference chamber 48 is increased. Alternatively, reference chamber 48 could include a predetermined amount of a factor for inducing coagulation, such that the clotting time of the portion of the blood sample in reference chamber 48 is decreased. More preferably, test chamber 46 also contains such a reagent, either wet or dried. Chamber 16 of FIGS. 2A and 2B could also contain such a reagent. In any case, the selection of the reagent for test chamber 46, reference chamber 48 or both would depend upon the type of test being performed and could easily be selected by one of ordinary skill in the art.

Sensor 42 is placed in contact with a receptacle 50 to perform the measurement of clotting time, as described for FIG. 2A. Receptacle 50 is also in electrical contact with capacitance measuring device 52, and is able to measure the capacitance between both sets of electrodes 18 from test chamber 46 and reference chamber 48. Similarly, a converter 54 should be able to separately convert each capacitance measurement to a digital signal. Both the test digital signal from test chamber 46, and the reference digital signal from reference signal 48, are then used by a processor 56 to calculate the clotting time.

The altered clotting behavior of the blood sample in reference chamber 48 is used to adjust the apparent clotting time of the blood sample as determined through test chamber 46. Such an adjustment acts as a control for any individual characteristics of the blood sample. These variations from the expected behavior of the blood sample can be compensated by the comparison of the amount of capacitance or the clotting time of the blood in reference chamber 48 and test chamber 46. Thus, the third preferred embodiment of the present invention as shown by device 40 is able to compensate for deviations from the theoretical clotting time of the blood sample in order to more accurately determine the true clotting time, or other coagulation characteristic, of the blood sample.

FIG. 2D shows yet another preferred embodiment of the present invention, which is substantially similar to the embodiment shown in FIG. 2A, except that electrodes 18 are formed within sensor receptacle 20, while test chamber 16 is formed on sensor 12.

As noted previously, both embodiments of the device of the present invention are based upon the determination of the movement of the blood sample through the test chamber and, if present, the reference chamber. Such a determination is performed by measuring the capacitance between the electrodes disposed on opposing sides or on the same side of the chamber, but insulated from the test liquid or simply located externally to the chamber. As the blood advances through the chamber, the volume of liquid in the chamber (and between the electrodes) will increase proportionally and will, likewise, cause a proportional increase in the electrical capacitance between the electrodes, as demonstrated for example in U.S. Pat. No. 5,720,733, incorporated by reference as if fully set forth herein.

For any of these embodiments, the chamber can be pretreated before the sample is analyzed, for example by soaking in a buffer containing a detergent and/or a hydrophilic polymer. Examples of such hydrophilic polymers include but are not limited to various kinds of polysaccharides, PVA (Poly Vinyl Alcohol), PVP (PolyVinyl Pyrrolidone), and proteins.

FIG. 3 is a schematic block diagram of yet another embodiment of the device of the present invention, featuring apertures in the cover of the sensor. These apertures are preferably placed in the cover of both the test and the reference chamber when both are present, or else simply in the cover of the test chamber.

According to one preferred design, a sensor 60 has a cover 62, sensor 60 being shown with cover 62 in place (left) and without cover 62 in place (right). As shown, cover 62 preferably features at least one aperture. More preferably, cover 62 features a plurality of apertures. A first aperture 64 is located over the area for inserting the sample when cover 62 is in place on top of sensor 60. Another aperture 66 and a plurality of smaller apertures 68 are dispersed along the length of a test/reference chamber 70 formed on sensor 60.

Apertures such as apertures 64, 66 or 68, alone or in combination, improve the degree of control exertable over the speed of advancement of the sample. In addition, when a reagent is present in the chamber, the apertures improve the extent of mixing of the sample with the reagent when such a reagent is present. As a result, the precision of the measurement is greatly improved. Indeed, increasing the extent to which the test chamber is uncovered slows the progression of the fluid of the sample, thereby improving the precision and the repeatability of the measurements. By slowing the progression of the fluid through the test chamber, a smaller and/or shorter device can be manufactured, which is in turn easier to handle, store and transport.

Section 2: Measurement of Resistance

Although the viscosity of the liquid sample, and in particular the clotting time of a blood sample, can be measured through capacitance as described previously, these properties of the sample can also be measured through resistance. This alternative embodiment of the present invention, which could optionally be incorporated in a single device with the previously described embodiment of the present invention, is described in greater detail below.

Figure 4:
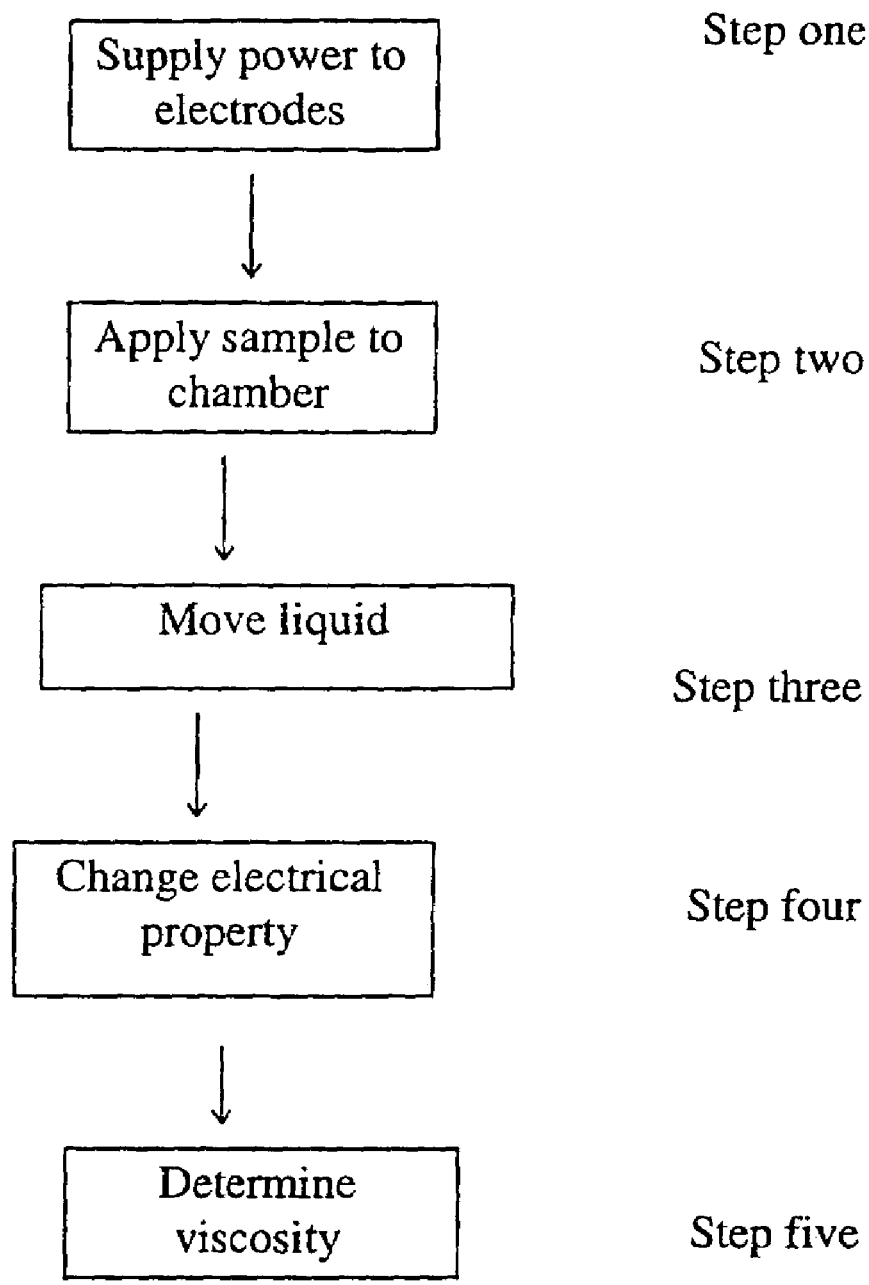
FIG. 4 is a flow chart of an exemplary method for determining the viscosity of a liquid through the measurement of resistance according to the present invention.

Referring now to the drawings, FIG. 4 shows a flow chart of an exemplary method for determining the viscosity of a liquid through the measurement of resistance according to the present invention. In step one, power is supplied to the electrodes. For example, a constant voltage could be applied across the electrodes. In step two, a sample of the liquid is placed at the entrance to a chamber with two electrodes. The lower surface of the chamber could be any suitable shape including, but not limited to, a square, a rectangle, a circle and an ellipse. Preferably, the chamber would feature a single capillary channel.

In step three, the liquid moves through the chamber through the action of a receiver, for example by capillary action, or by application of a vacuum, by gravity, or through mechanical or osmotic pressure, thereby increasing the surface area of the electrodes which is covered by the liquid. The vacuum could be applied by the presence of a suction device which is an example of the receiver. The capillary action could be caused by a capillary structure such as a capillary depth of the chamber, and/or a narrow channel shape of the chamber. The capillary depth of the chamber would be a depth selected to ensure that the liquid would enter the chamber through the capillary action.

In step four, the movement of the liquid causes an electrical property to alter as the covered surface area of the electrodes increases. For example, the measured current could increase, or the resistance could decrease. In step five, the alteration of the electrical property is used to determine the viscosity of the liquid sample.

This embodiment of the method of the present invention could be used to measure the viscosity of a blood sample as it clots, for example. The blood sample would be taken from the patient and then placed at the entrance to the chamber, as described previously. The clotting time could then be determined by measuring the current after a fixed time period had elapsed, or by measuring the period of time required to reach the maximum current, for example. In either case, the length of time required for the blood sample to clot would be directly related to the surface area of the electrodes covered by the sample before clotting occurred. For example, if the current was measured after a fixed time period had elapsed, the amount of current would increase as the clotting time also increased, as this would permit the blood sample to travel farther down the chamber before clotting occurred. Similarly, if the time period required to reach the maximum current was measured, this time period would increase as the clotting time also increased. Thus, as the clotting time increased, the surface area of the electrodes covered by the sample before clotting occurred would also increase.

Although the description of exemplary devices for measuring the viscosity of a liquid sample according to the present invention is specifically drawn to devices for determining the clotting time of a blood sample, it is understood that this is for the sake of clarity only and is not meant to be limiting. As noted previously, the method and device of the present invention could also be used to determine the viscosity of substantially any type of liquid sample, as such viscosity is directly related to the surface area of the electrodes covered by the sample as the liquid sample moves through the chamber.

Figure 5A:
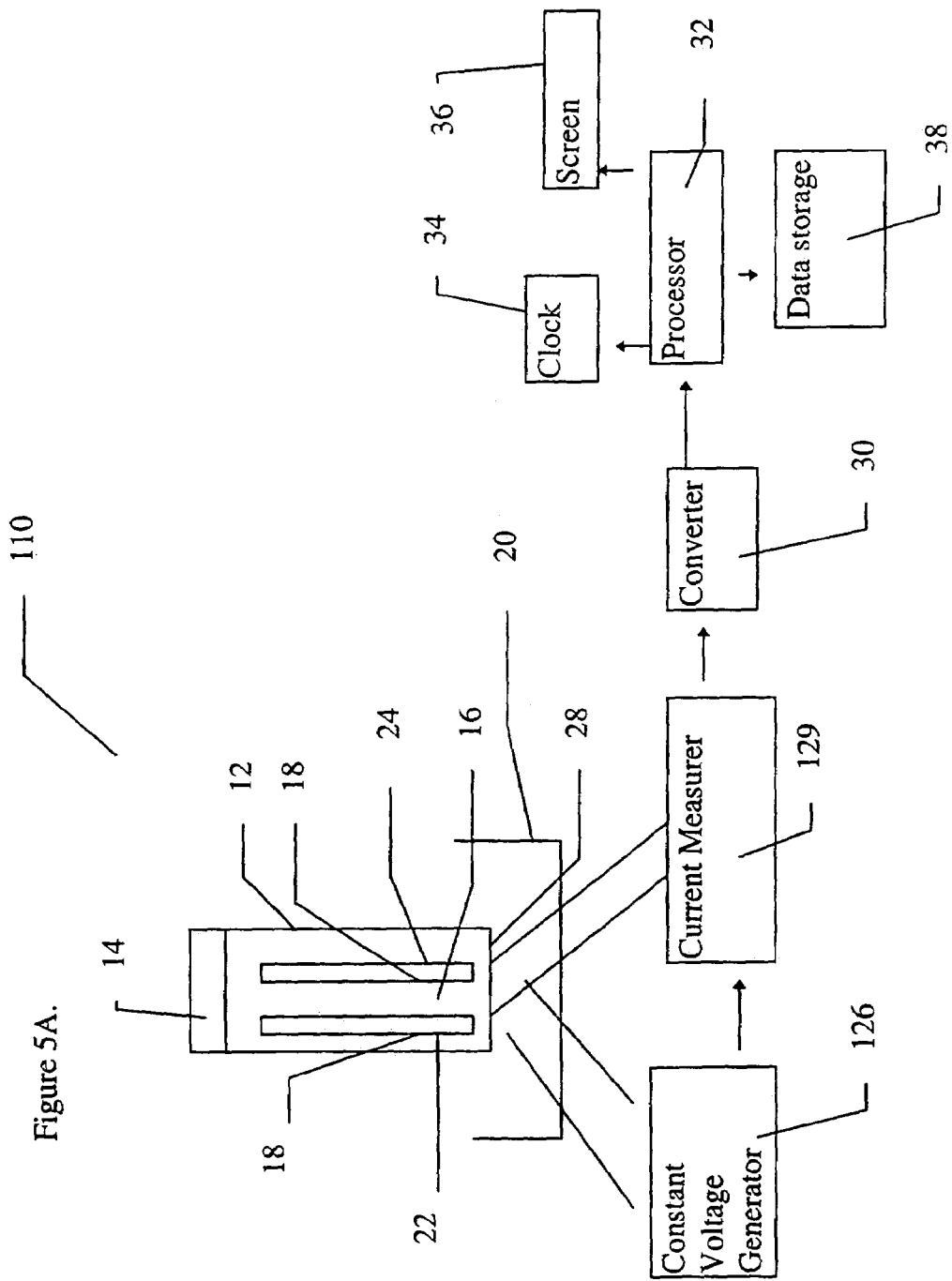
FIGS. 5A–5C are schematic block diagrams of exemplary devices for the determination of clotting time by resistance according to the present invention.
Figure 5B:
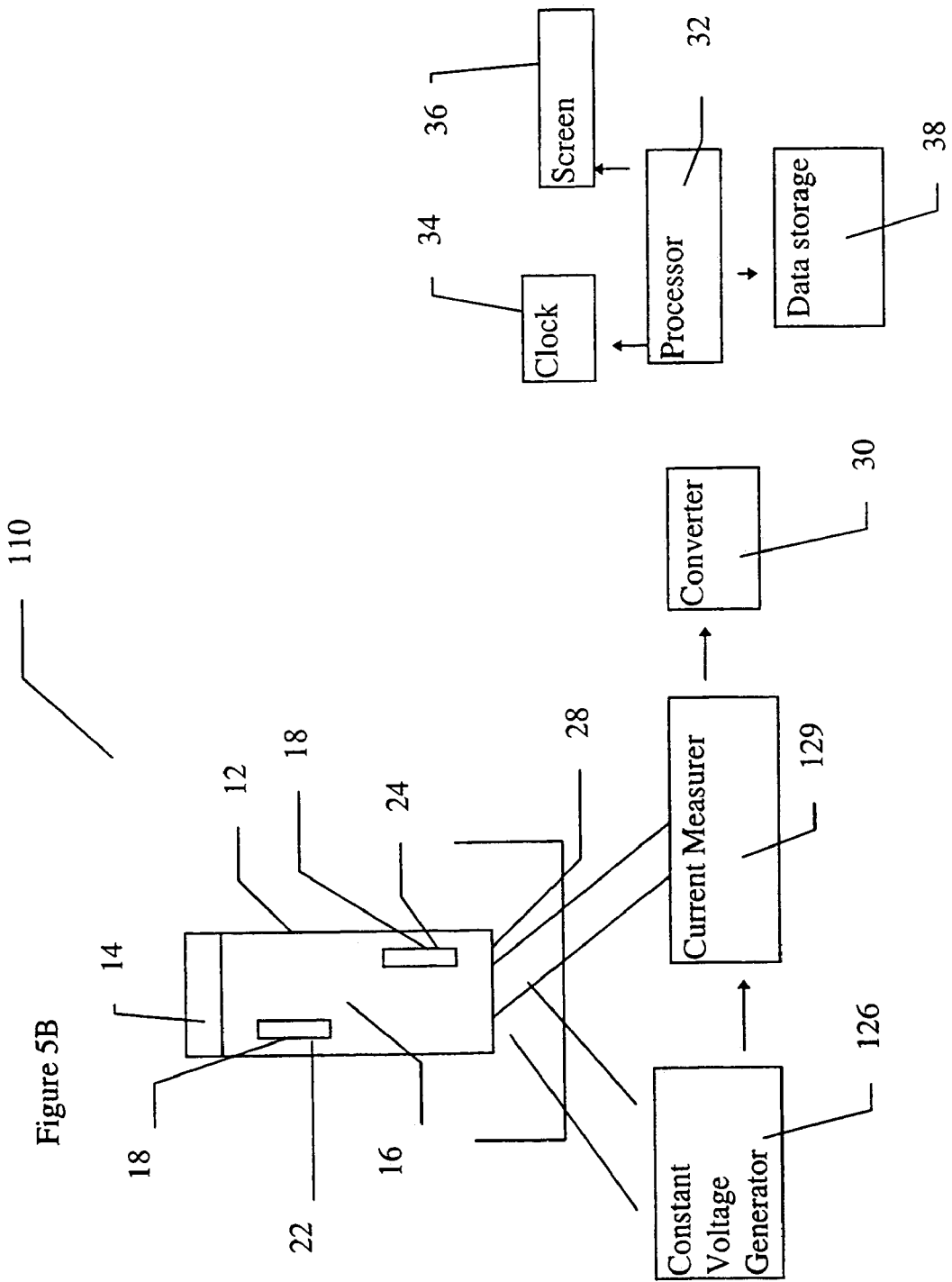
Figure 5C:
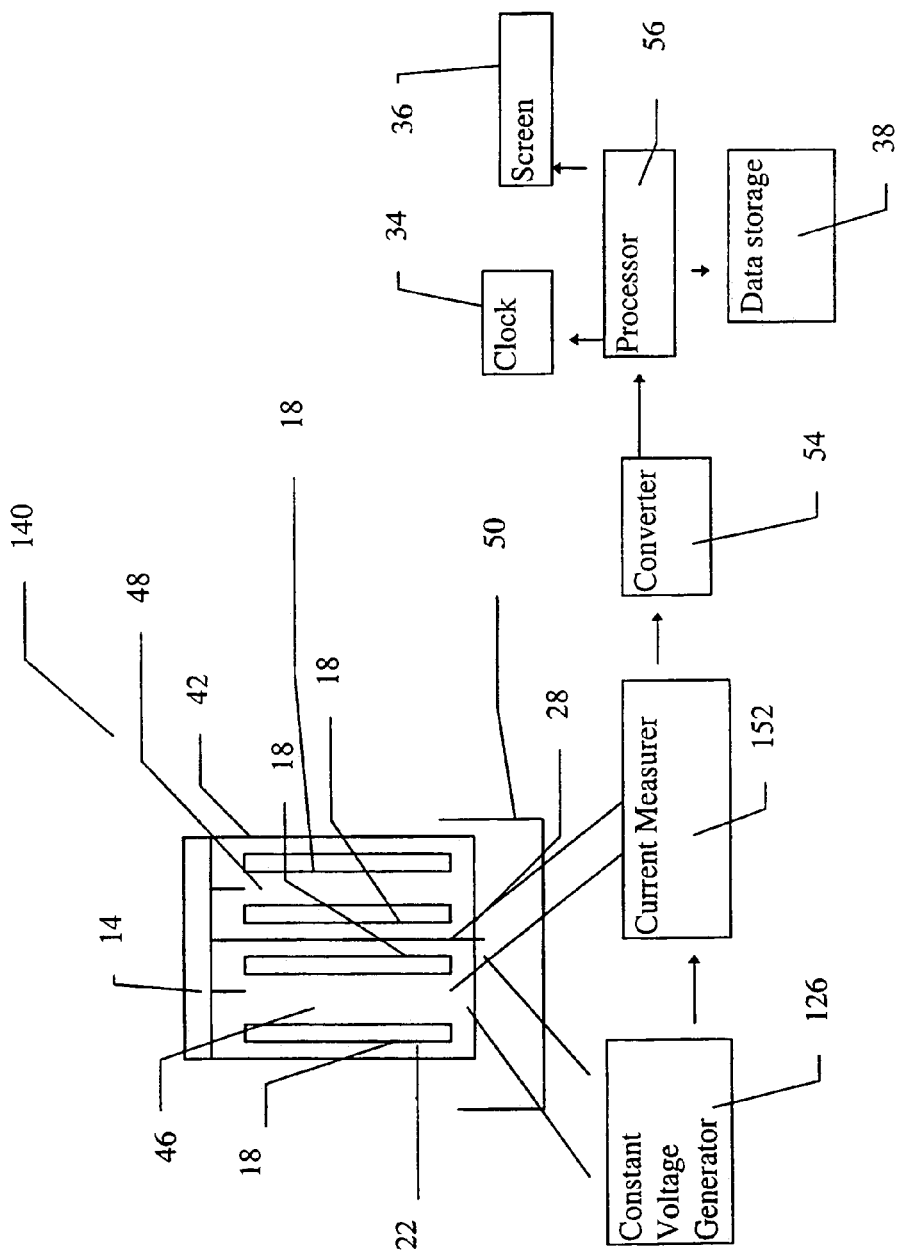

FIGS. 5A–5C are schematic block diagrams of exemplary devices for the determination of clotting time by resistance according to the present invention, which are similar in certain respects to FIGS. 2A–2D described previously. Those features which are identical to the devices of FIGS. 2A–2D are labeled with the same reference numbers in FIGS. 5A–5C.

FIG. 5A shows a first embodiment of an exemplary device for determining the viscosity of a liquid, such as a blood sample, by the measurement of resistance. A clotting diagnostic device 110 is shown, which differs from clotting device 10 of FIG. 2A in several respects. First, the power source which is in electrical contact with sensor receptacle 20 is preferably a constant voltage generator 126. Constant voltage generator 126 is attached to both electrodes 18. As shown, first electrode 22 is the positive electrode and second electrode 24 is the negative electrode, but polarity may be reversed without affecting the functionality of the device.

Second, preferably opposing end 28 of sensor 12 is first placed in contact with sensor receptacle 20 and then voltage is applied to electrodes 18 from constant voltage generator 126. In this embodiment, device 110 could be a kit for determining the clotting time of the blood sample from the patient in the home testing environment.

This particular mode of operation is more preferred because the application of the blood sample can automatically trigger the timing function. For example, when sensor 12 is placed in contact with sensor receptacle 20 before a blood sample has been applied, the measured current would be approximately zero. As soon as the blood sample was applied, the measured current would immediately and rapidly increase, enabling device 110 to automatically detect the presence of the blood sample.

As blood sample flows through test chamber 16, the liquid contacts both electrodes 18, one on either side of test chamber 16. Such contact enables electrical current to move from first electrode 22 to second electrode 24. As more liquid flows into test chamber 16, an increasing amount of electricity flows from first electrode 22 to second electrode 24, thus increasing the amplitude of the current.

As electrical current flows from first electrode 22 to second electrode 24, the amplitude of the current is measured by an exemplary current measuring device 129, which is the second important difference from device 10 of FIG. 2A. Since the current is measured at a fixed voltage, the changes in resistance as liquid flows over first electrode 22 and second electrode 24 could also be measured, provided the applied voltage is sufficiently high to result in an easily detectable current. Indeed, glucose meters for the home testing environment also measure current. Thus, the measurement of current is preferred in a device for the home testing environment since the electronic equipment required is more suitably robust.

After measuring the current, current measuring device 129 then converts the measured current to voltage. The analog voltage is then converted to a digital signal by converter 30, and the digital signal is then sent to a processor 32 for analysis of the signal and the calculation of the clotting time from the signal. Processor 32 again includes instructions for calculating the clotting time from the signal. Again, processor 32 also includes a clock 34 for accurately measuring time. Such clocks suitable for micro-processors and other computational devices are well known in the art. Processor 32 could be a dedicated microprocessor with ROM (read-only memory) memory for storing the instructions, for example. Such current measuring circuits already exist in portable electrochemical blood glucose meters, such as those distributed by Bayer, under the trade name of Glucometer Elite™, and by Medisense, under the trade name Exactech™.

The clotting time could be calculated in a variety of ways. For example, the blood sample could be allowed to flow through test chamber 16 until clotting had occurred, at which point blood sample would cease to flow. The cessation of blood flow through test chamber 16 could be determined by noting the time point at which the amplitude of the current reaches a maximal value. The clotting time would then be determined according to this time point. Alternatively and preferably, the amplitude of the current could be measured at a fixed time point, after a predetermined period of time had elapsed from the time at which sensor 12 was placed in contact with sensor receptacle 20.

According to yet another preferred embodiment of the device of the present invention for measuring the viscosity of a liquid through the determination of resistance, shown in FIG. 5B, electrodes 18 could be arranged such that neither electrode 18 extends along substantially a majority of, or substantially the entirety of, the length of test chamber 16. Instead, preferably, both electrodes 18 are relatively short so as to extend only along a portion of test chamber 16, this portion being substantially shorter than the majority of the length of test chamber 16, in an arrangement which is similar to that shown in FIG. 2B.

In this preferred embodiment, the time required to close the circuit is determined in order to calculate the clotting time, rather than the amount of current. The time required to close the circuit is the period of time required for the blood sample to proceed from first electrode 22, which is closer to sample area 14, to second electrode 24. This embodiment has the advantage of simplified electrical measurement since the measurement of amplitude is not important, while the time period required for closing the circuit is easily and inherently determined by any microprocessor or a timer circuit which are well known in the art.

FIG. 5C is a block diagram of a third exemplary embodiment, in which the device of the present invention is able to compare the clotting time of the blood sample with the behavior of a control sample. In this embodiment, a clotting diagnostic device 140 is similar to clotting diagnostic device 40 of FIG. 2C. However, receptacle 50 is now in electrical contact with constant voltage generator 126. A current measuring device 152 is able to receive current from both sets of electrodes 18 from test chamber 46 and reference chamber 48 and to convert the measured current to voltage. Similarly, an analog to digital converter 54 should be able to separately convert each analog signal to a digital signal. Both the test digital signal from test chamber 46, and the reference digital signal from reference signal 48, are then used by processor 56 to calculate the clotting time.

The altered clotting behavior of the blood sample in reference chamber 48 is used to adjust the apparent clotting time of the blood sample as determined through test chamber 46. Such an adjustment acts as a control for any individual characteristics of the blood sample. These variations from the expected behavior of the blood sample can be compensated by the comparison of the amplitude of the current or the clotting time of the blood in reference chamber 48 and test chamber 46. Thus, the third preferred embodiment of the present invention as shown by device 140 is able to compensate for deviations from the theoretical clotting time of the blood sample in order to more accurately determine the true clotting time, or other coagulation characteristic, of the blood sample.

As noted previously, this embodiment of the device of the present invention are based upon the determination of the movement of the blood sample through the test chamber and, if present, the reference chamber. Such a determination is performed in this embodiment by measuring the electrical current passing through the electrodes disposed on opposing sides or on the same side of the chamber. As the blood advances through the chamber, the surface of the electrodes covered by the blood will increase proportionally. If a constant voltage is applied to the electrodes, the electrical current will be proportional to the resistance of the system, which includes the components of the device and the blood sample itself. Such proportionality can be demonstrated by the following equations:

$$V=iR$$

where V is voltage, R is resistance and i is current. This equation can be rearranged to:

$$i=V/R$$

However, resistance can be determined as follows:

$$R=\rho L/A$$

where $\rho$ is the specific resistance of the material, L is the distance between the two electrodes and A is the area of the electrodes. Therefore, $$i=VA/(\rho L)$$

such that $\rho$ and L are constant. If voltage is then held constant, current (i) is proportional to the surface area (A) of the electrodes covered by the blood sample and hence to the clotting time of the blood sample.

EXAMPLE 1

Construction and Testing of a Clotting Time Device

The device, including the sensor, was constructed according to the first example of this embodiment of the device of the present invention, as shown in FIG. 5A. The sensor was constructed from a flat plastic base card, by building an approximately 1.5 mm wide and approximately 20 mm long capillary channel over the two conductive carbon tracks. The sides of the channel were built from double sided adhesive tape, about 200 microns deep. The channel was covered with a section of transparent polyester film. The arrangement was designed to permit a reference portion of a five microliter blood sample to travel along the entire length of the capillary channel, while a second portion of the same sample remains at the sample origin, thus preventing limitation of measurement by the sample size.

The electrodes were then attached to a standard voltage generating device, and the resulting current was then measured by a standard device for measuring current or voltage. Both of these devices are well known to those of ordinary skill in the art. It should be noted that this sensor was intended as an example for experimental testing only and was not meant to be limiting in any way.

For the specific tests described below, the volume of the blood sample was five microliters and a 1.5 V voltage was applied from the voltage generating device.

Figure 6A:
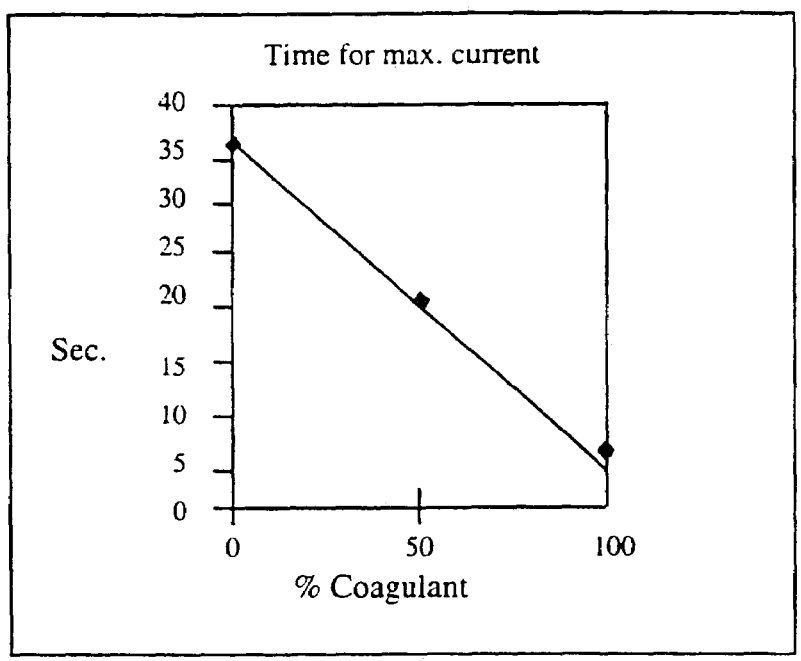
Figure 6B:
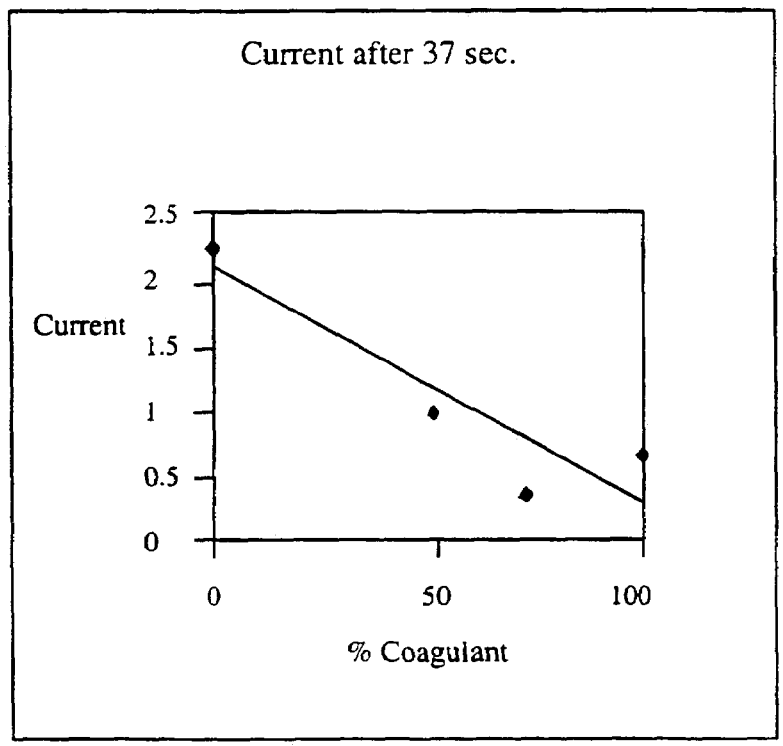
Figure 6C:
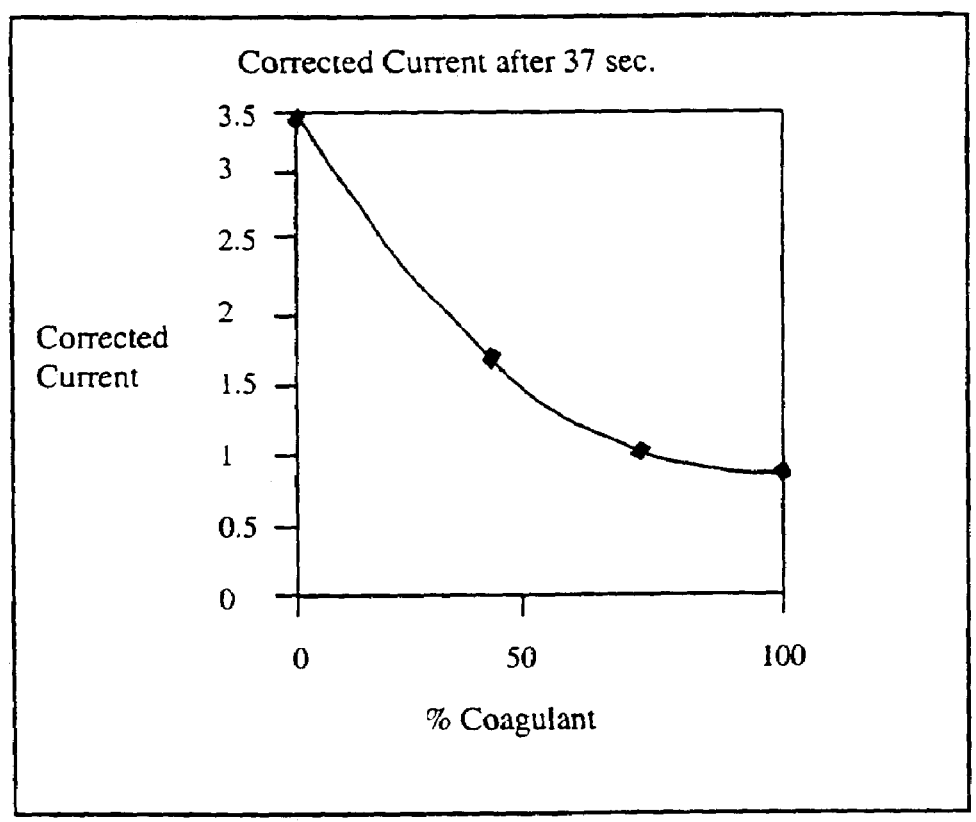

Variation between blood samples was simulated by generating a series of blood samples to which varying amounts of coagulants were added. FIGS. 6A–6C show the effect of the addition of coagulant to blood samples on the measurement of current by the device. FIG. 6A shows the decrease in the amplitude of the current (micro-amperes) as the percentage of coagulant added to the sample is increased. The amplitude of, the current was measured 37 seconds after the sample was placed in the sensor. FIG. 6B shows the decrease in the elapsed time (shown in seconds) required for the maximum current to be reached as the percentage of coagulant added to the sample is increased. Clearly, both the current at 37 seconds and the elapsed time required for the maximum current is related to the amount of coagulant added to the sample.

FIG. 6C shows the corrected measured current from FIG. 6A. The correction was performed as follows. The current (I) was measured at time zero ($I_0$), as soon as the blood sample was placed on the sensor (the sensor was already attached to the remainder of the device). The current was then measured again after one second had elapsed ($I_1$). The time period of one second was chosen so as to measure the current after a minimum time period had elapsed and before coagulation had started. Next, the average of $I_0$ and $I_1$ was determined ($I_a$). Finally, for each point of the transient curve of FIG. 6A ($I_t$), the correction was performed as follows:

$$I_{corrected} = (I_t - I_a)/I_a$$

Such a method is an example of a method for correcting the measured current without using a reference chamber.

EXAMPLE 2

Construction and Testing of a Clotting Time Device with Dried Reagents

An exemplary device of the present invention was also constructed according to the first embodiment of the device of the present invention, as shown in FIG. 5A. In this case, however, coagulation reagents (Sigma Chemical Co) were dried in one area of the sensor. It should be noted that this device was also intended as an example for experimental testing only and was not meant to be limiting in any way.

Figure 7A:
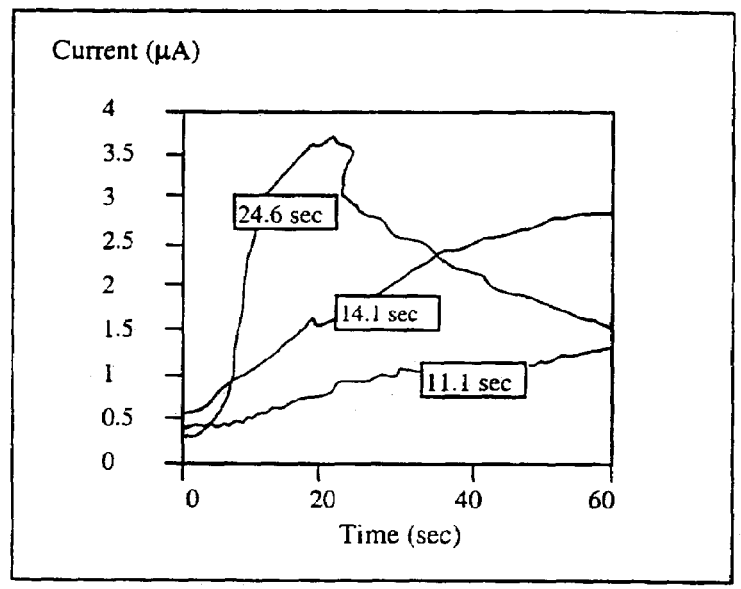
FIGS. 7A and 7B show the variation of the current for three different blood samples from patients undergoing anticoagulant therapy.

FIG. 7A shows the variation of the current (micro-amperes) over time (seconds) for three different blood samples from patients undergoing anticoagulant therapy. These samples had different clotting times, which were measured as prothrombin time. Prothrombin time was determined both by the sensor, as shown in the graph, and with a standard reference method, employing an ACL1000 instrument. The clotting times obtained with the standard instrument are shown inside rectangles, attached to each of the current transient curves of the respective samples.

The measurement of prothrombin time with the ACL1000 instrument involved the separation of the plasma from the whole blood. Next, the plasma was mixed with a coagulant reagent mixture, which includes tissue factors and calcium ions. An equivalent coagulant reagent mixture was also dried onto the sample area of the sensor of the present invention. The clotting time was then determined by measuring the change in optical density of the sample with the ACL1000 instrument.

With regard to the curves determined with the device according to the present invention, clearly, the time required to reach the maximum measured current, which occurs at the time of clotting of the blood, was different for blood samples with different clotting times as determined by the ACL1000 instrument.

Figure 7B:
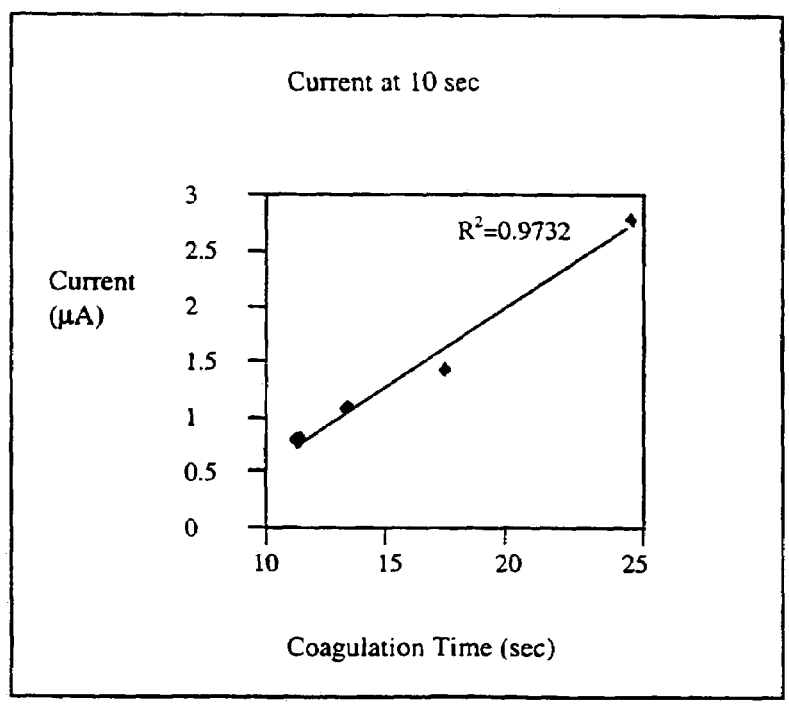

FIG. 7B shows the quantitative relationship between the measured current 10 seconds after the blood sample was applied to the sensor inserted in the device of the present invention, and the coagulation time as determined by the standard reference method. Clearly, there is a directly proportional relationship between the current measured 10 seconds after application of the sample and the coagulation time, as determined by the reference method.

EXAMPLE 3

Construction and Testing of a Clotting Time Device with Dried Reagents

An exemplary device of the present invention was also constructed according to the first embodiment of the device of the present invention, as shown in FIG. 5A. However, as further detailed below, certain modifications were made to the device. In particular, the carbon electrodes were subjected to a pretreatment, and a particular formulation of coagulation reagents was dried onto the sample area of the sensor of the present invention. It should be noted that this device was also intended as an example for experimental testing only and was not meant to be limiting in any way.

The preparation of this exemplary device according to the present invention was as follows. First, the carbon electrodes were cut and then pretreated by soaking in a buffer containing 0.1 M $Na_2CO_3$, 10 mg/ml BSA and 0.1% Tween-20 for 10 minutes at room temperature. Next, the electrodes were washed four times by dipping in distilled water. The electrodes were then dried over a hot plate at 75° C.

The coagulation reagents were then prepared from lyophilized recombinant human thromboplastin reagent Innovin® (Dade International, USA). The active ingredients of Innovin® are a mixture of dried recombinant human tissue factor, which starts the coagulation cascade, and calcium ions. These active ingredients promote coagulation of the blood sample.

The contents of a 10 ml vial of Innovin® was resuspended with 2.5 ml of distilled water. This was supplemented with 200 mg/ml Mannitol (BDH, United Kingdom) and 0.1% Bioterge AS 40 (Stepan Europe, France).

The sensor of the present invention was then constructed with a modified spacer assembly as follows. First, the spacer was created by cutting a piece of 210 micron double coated polyester film (MS1182, Duramark; USA) to the desired shape. Squares of paper (5 mm by 7 mm) were then cut from Kimwipes® EX-L (Kimberly-Clark, USA) and were attached to the spacer at the sample area, such that substantially the entirety of the sample area up to the beginning of the capillary channels was covered with paper, to form the spacer assembly.

The spacer assembly was then attached to the electrodes. Eight microliters of reagent were applied to the paper lining the sample area of the spacer assembly and dried overnight at 37° C. in a turbo oven (Series 9000, Scientific). After drying, a piece of a transparency film (9 mm by 48 mm) was attached to the remaining free adhesive area of the spacer assembly, thus creating the capillary channels through which the blood sample flows.

The determination of clotting time by using this exemplary device was performed by inserting the sensor into the apparatus for measuring current. The power supply was set to supply 1500 mV of electricity to the electrodes. Next, a blood sample of 30 microliters was added to the paper at the sample area of the sensor, where the sample mixed with the dried reagent. The addition of the paper to the sample area had the advantage of promoting better mixing of the blood sample with the dried reagent material. Paper is an example of a substantially porous material which preferably at least partially covers the sample area in order to promote mixing of the blood and dried reagents. As for previous embodiments, the blood sample then flowed from the sample area through the capillary channels.

As soon as the blood sample contacted the electrodes, the apparatus began the measurement of elapsed time. Substantially simultaneously, the supply of electricity from the power source to the electrodes was temporarily suspended for about 90 seconds, until the blood sample ceased flowing forward through the capillary channel. At that moment, electricity was again supplied to the electrodes for about 4 seconds and the current was recorded.

Table 1 below shows the current measured 4 seconds after the electricity supply to the electrodes was re-established.

The International Normalized Ratio is an adjusted value of clotting time, which is calculated as $R^{ISI}$, wherein R is the ratio of the prothrombin time determined for the blood sample and the mean of prothrombin times for normal subjects, and ISI is the International Sensitivity Index, which is a measure of the potency of the thromboplastin reagent employed in the assay. The value of ISI for Innovin® was provided by the manufacturer.

TABLE 1

Current Measured after Clotting

| Sample Number | International Normalized Ratio | Current (micro-amperes) |
|---|---|---|
| one | 0.98 | 0.281 ± 0.28 |
| two | 3.48 | 3.821 ± 0.071 |

As shown from these two samples, clearly the amount of current measured after clotting has occurred is directly related to the time of clotting. The device of this Example has the advantage of potentially greater reproducibility of results, as well as the ability to provide accurate results regardless of variations in the surface of the plastic substrate and the material of the electrodes.

EXAMPLE 4

Determination of Clotting Time with a Sensor Strip

An exemplary device of the present invention was also constructed according to the first embodiment of the device of the present invention, as shown in FIG. 5A. However, as further detailed below, certain modifications were made to the device. In particular, a nylon mesh was placed over the spacers in order to create the capillary channel, as shown in FIG. 8. It should be noted that this embodiment could be altered to include the cover with apertures of FIG. 3. Similarly, the cover with apertures of FIG. 3 could be replaced by the mesh shown in FIG. 8. The device was prepared as follows.

1. First the sensor strip was prepared. Clotting time sensor strips were constructed from the following parts, which are depicted in FIG. 8. A Lexan® polycarbonate base card 154 featured two printed carbon electrode tracks 156. For the purposes of this example, the dimensions of base card 154 were approximately 60 mm×5 mm, although of course these dimensions could be altered. A spacer 158 was die-cut from a 2-mil thick polyester sheet, double coated with an acrylic pressure sensitive adhesive (Adhesives Research, type 7810). Spacer 158 was attached to base card 154 so that the open slit in spacer 158 was centered over the space between electrodes 156, thereby exposing a part of both electrodes 156. The width of the slit was 1 mm and its length was 30 mm. The reagent/specimen area had a width of 3 mm and a length of 10 mm. Next, a nylon mesh 160 (Nybolt 95T from Sefar, Ruschlikon, Switzerland) was attached to the top of spacer 158, thus creating a capillary channel.

For the purposes of testing the device shown in FIG. 8, a 10 mL vial of Innovin® (a PT reagent, supplied by Dade International, Inc, Miami, Fla., USA) was dissolved in 3.0 mL of 20% w/v mannitol, 0.35% w/v Pluronic F-68. Five µL of the mixture was spread over the reagent area (the wide part of the channel, as defined by the spacer) and dried at a temperature of 50° C. in a turbo oven (American Scientific products Model Dk-62).

All measurements were then performed at room temperature (23–26° C.). Citrated whole blood samples were obtained from a clinic. The INR value of all specimens was determined with an MLA-1000 apparatus (Medical Laboratory Automation, Inc., Pleasantville, N.Y., USA), which was used as the reference method.

Figure 9:
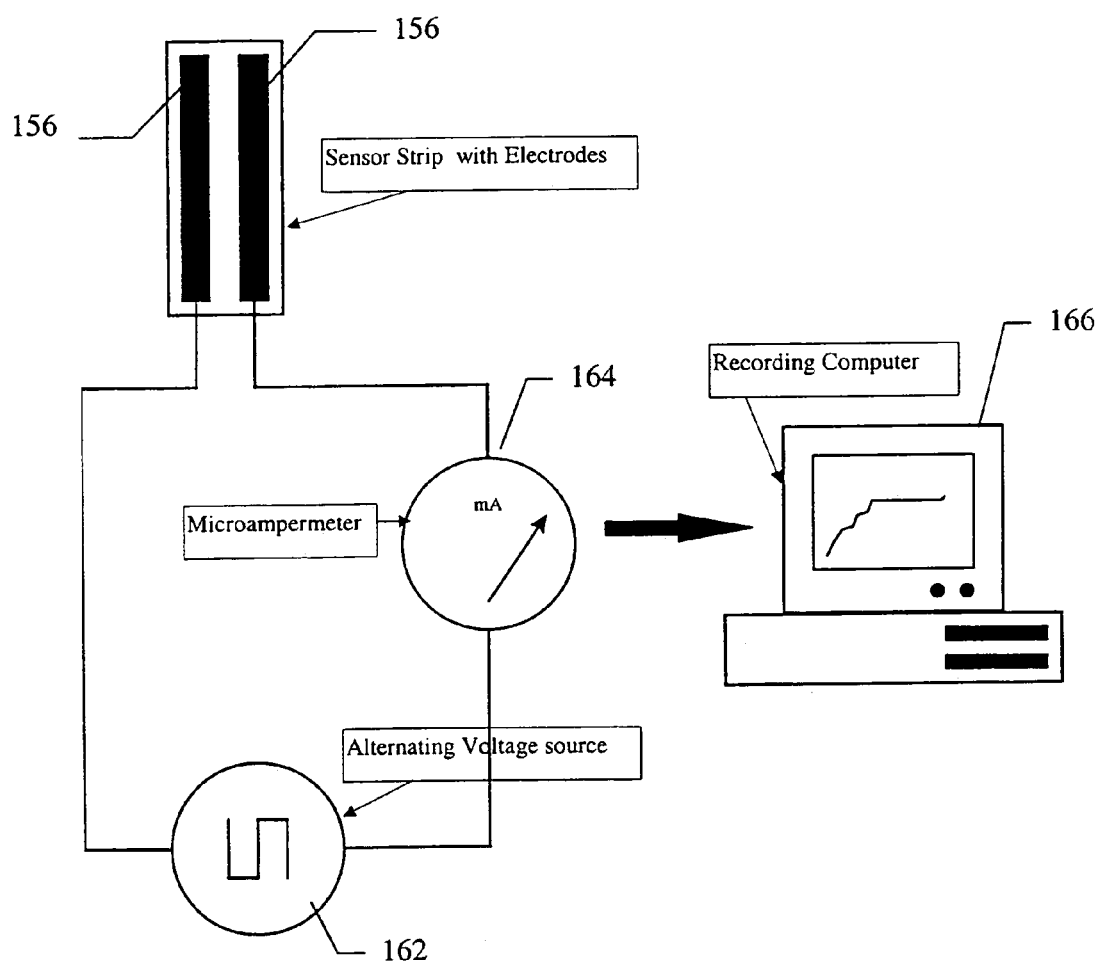
FIG. 9 shows a schematic block diagram of the circuit for testing the device of FIG. 8.

Amperometric determination of the clotting time with the sensor strip was then performed by connecting electrodes 156 in the sensor to a Wavetek model 130-s-396 function generator, which was adjusted to deliver a 3.5 Volts, 10,000 Hz square wave AC. The current flowing through the circuit was measured with a data logging Thurlby Thandar Instruments (Huntington, Cambridgeshire, UK) model 1705 multimeter. A schematic drawing of the circuit is depicted in FIG. 9, with electrodes 156 connected to an alternating voltage source 162 and to a microampermeter 164. Microampermeter 164 was in turn connected to a recording computer 166.

Figure 10A:
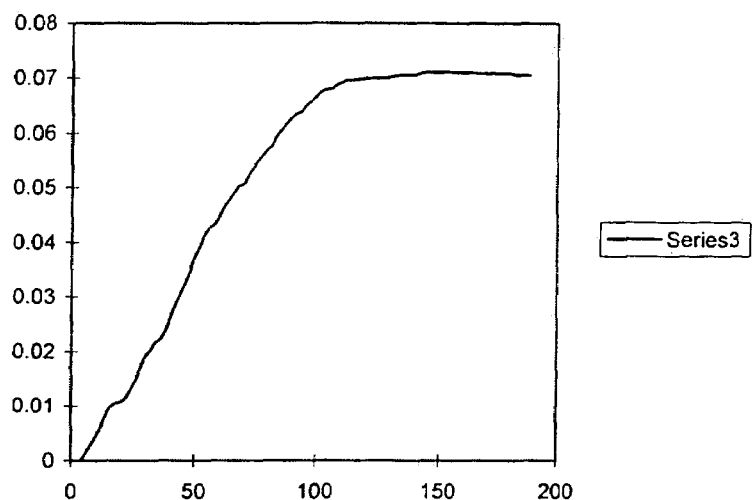
FIGS. 10A and 10B show examples of transients for different INR values for the device of FIGS. 8 and 9.
Figure 10B:
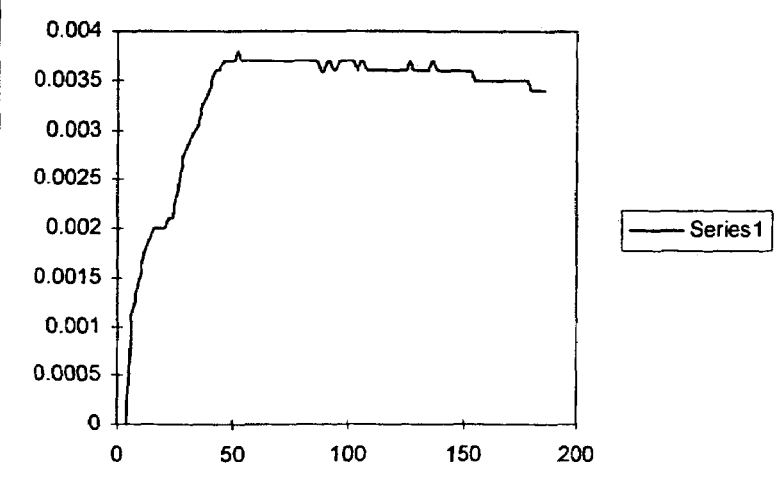
Figure 11A:
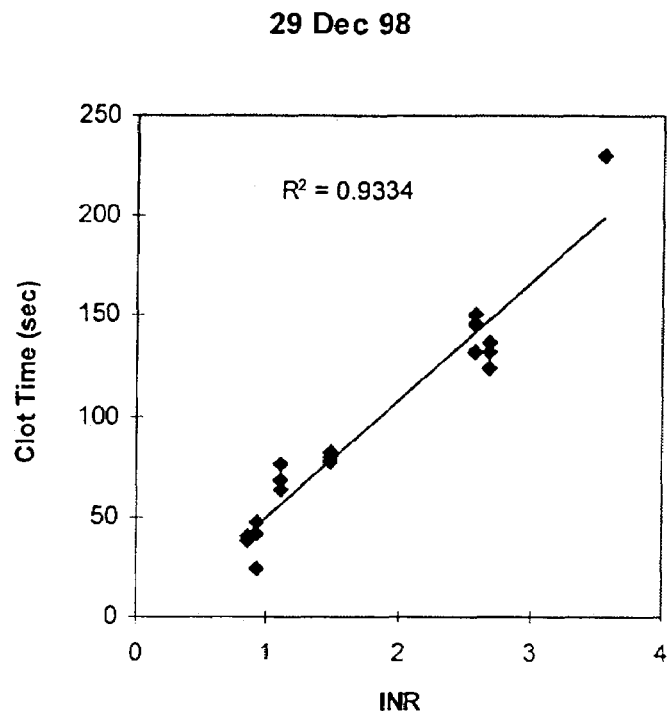
FIGS. 11A–11C depict the correlation between the clotting time values, as obtained with the sensor strip of the invention, and the INR values, as determined by the reference method.
Figure 11B:
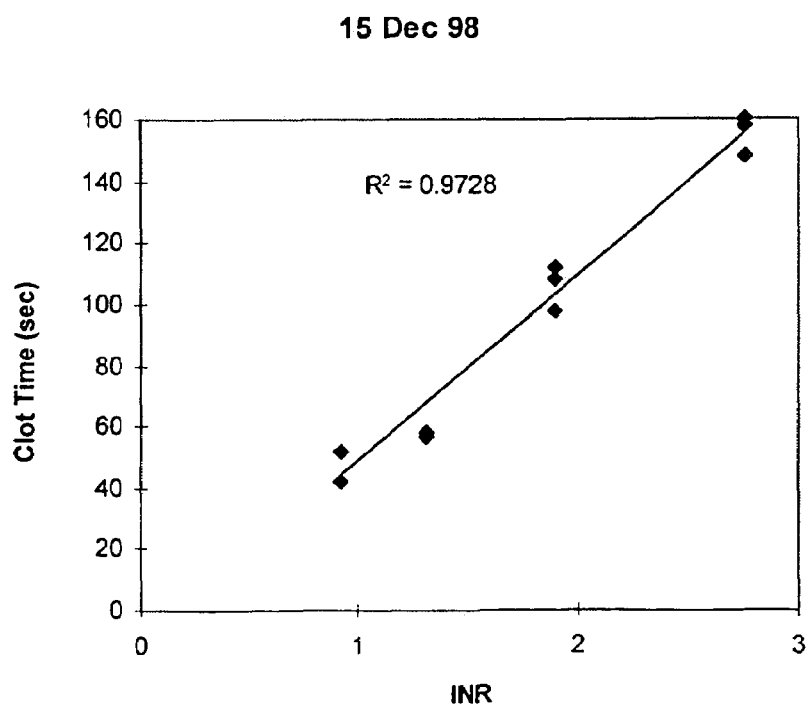
Figure 11C:
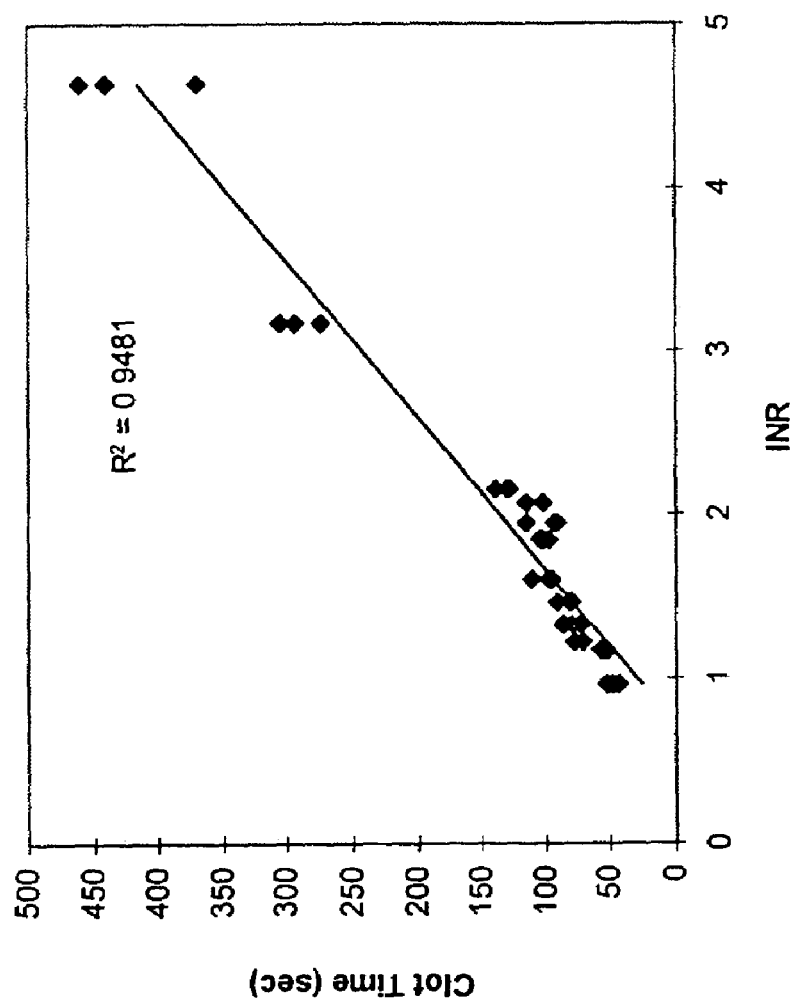

To perform a coagulation time measurement, voltage source 162 and to microampermeter 164 were activated so that 0.5 Hz data logging started on microampermeter 164. Immediately afterward, a 15 µL specimen was applied to the reagent area. Logging of the current measurement continued for 200 seconds. Thereafter, the data was transferred through a serial connection to recording computer 166 for plotting the current vs time transient. Examples of transients for different INR values are presented in FIGS. 10A and 10B. The coagulation time of the specimen was determined according to the time point at which the current stopped rising. FIGS. 11A–11C depict the correlation between the clotting time values, as obtained with the sensor strip of the invention, and the INR values, as determined by the reference method.

The values for the prothrombin time were plotted against the INR values determined by the MLA-1000 apparatus. It is clear that the sensor strip of the present invention demonstrated a linear correlation between the measured clotting time and the reference INR value.

Section 3: Detection of a Receptor/Ligand Interaction

An additional preferred embodiment of the device of the present invention could measure a receptor/ligand reaction as follows. A clotting factor would be attached to a receptor or ligand to form a combined clotting factor-acceptor. Hereinafter, the term "acceptor" refers to either a receptor or a ligand. Examples of acceptors include but are not limited to antigen, antibody, nucleic acid probe and lectin. The clotting factor-acceptor complex would then be placed relative to the blood sample such that the reactivity of the clotting factor would then be modulated by the recognition reaction between the acceptor and the corresponding ligand or receptor, respectively. Preferably, the calculation of the alteration in blood clotting time would be determined by comparing the clotting time required for a reference portion of the blood sample which was exposed to the acceptor/coagulation factor combination, to the time required for a second portion which was not exposed to the combination.

For example, if the acceptor was an antigen and the clotting factor was an anti-coagulant, the anti-coagulant would be hidden from the blood sample substantially only if the blood sample contained an antibody which recognized the antigen. Such hiding would decrease the time required for clotting of the blood. The degree to which the blood clotting time decreased could be used to quantitate the amount of antibody present in the blood sample. This preferred embodiment of the device would still measure the clotting of blood according to the amount of current passing through the sample, either when measured after a fixed period of time has elapsed, or by determining the elapsed time required for the maximum measured current to be reached.

The same principle for detection of receptor-ligand reaction can be realized through other viscosity modulating systems, which are well known in the art. Such systems include: dextran and dextranase, DNA and DNase.

It will be appreciated that the above descriptions are intended only to serve as examples, and that many other embodiments are possible within the spirit and the scope of the present invention.

What is claimed is:

1. A device for measuring a viscosity of a sample of a liquid, the device consisting essentially of:
   (a) a test chamber for receiving a test portion of the sample of the liquid, said test chamber featuring walls for defining an interior space of said test chamber;
   (b) a pair of electrodes disposed on said walls of said test chamber
   (c) a capacitance measuring circuit for measuring a capacitance of said test portion of the sample within said test chamber between said electrodes, such that said capacitance directly reflects a volume occupied by said test portion of the sample of the liquid; and
   (d) a clock for measuring a predetermined time period after said test chamber receives said liquid, such that said amount of said capacitance is determined after said predetermined time period has elapsed.

2. The device of claim 1, further comprising:
   (e) an insulator for insulating said pair of electrodes such that said pair of electrodes are prevented from being in contact with the sample of liquid.

3. The device of claim 2, wherein said insulator includes said walls of said test chamber, such that said pair of electrodes is disposed externally to said walls.

4. The device of claim 1, wherein a lower surface of said test chamber has a shape selected from the group consisting of rectangular, square, circular and elliptical.

5. The device of claim 1, further comprising:
   (e) a receiver for causing said test chamber to receive said test portion of the sample of the liquid, said receiver being selected from the group consisting of a pump for pumping said test portion into said test chamber and a suction device for creating a vacuum.

6. The device of claim 1, wherein said test portion of the sample of the liquid enters said test chamber from the force selected from the group consisting of gravity, mechanical pressure and osmotic pressure.

7. The device of claim 1, wherein said test portion of the sample of the liquid enters said test chamber from a capillary force induced by a capillary structure of said test chamber.

8. The device of claim 1, wherein said capillary structure is selected from the group consisting of a capillary depth of said test chamber, and a narrow channel shape of said test chamber.

9. The device of claim 1, wherein said test chamber features a single capillary channel.

10. The device of claim 1, wherein the sample of the liquid is selected from the group consisting of whole blood, plasma and serum.

11. The device of claim 10, wherein the sample of the liquid is whole blood.

12. The device of claim 11, wherein a change in the viscosity of said whole blood is caused by coagulation, such that a volume of said test chamber being occupied by said test portion of said whole blood is determined according to said coagulation.

13. The device of claim 12, wherein said test chamber features at least one coagulant agent being in contact with said test portion of said whole blood, said at least one coagulant agent altering a clotting property of said test portion of said whole blood.

14. The device of claim 13, wherein said coagulant agent is an anti-coagulant, such that said test portion of said whole blood clots slower said reference portion of said whole blood.

15. The device of claim 13, wherein said coagulant agent is a pro-coagulation factor, such that said test portion of said whole blood clots faster than said reference portion of said whole blood.

16. The device of claim 13, wherein said at least one coagulant agent is dried onto said test chamber.

17. The device of claim 13, wherein said at least one coagulant agent is a liquid droplet placed onto said test chamber.

18. The device of claim 1, further comprising:
   (e) a cover for covering said test chamber, said cover featuring a mesh.

19. The device of claim 1, wherein said clock automatically begins measuring said predetermined time period after said test chamber receives said whole blood.

20. A device for measuring a viscosity of a sample of a liquid, the device consisting essentially of:
   (a) a test chamber for receiving a test portion of the sample of the liquid, said test chamber featuring walls for defining an interior space of said test chamber;
   (b) a pair of electrodes disposed on said walls of said test chamber;
   (c) a capacitance measuring circuit for measuring a capacitance of said test portion of the sample within said test chamber between said electrodes such that said capacitance directly reflects a volume occupied by said test portion of the sample of the liquid; and
   (d) a clock for measuring a period of time required for said amount of said capacitance to reach a predetermined level.

21. The device of claim 20, wherein said clock automatically begins measuring said period of time after said test chamber receives said whole blood.

22. The device of claim 1, further comprising:
   (e) a disposable sensor, wherein said test chamber and said electrodes are located on said sensor, such said whole blood is placed on one end of said disposable sensor; and
   (f) a sensor receptacle for receiving an opposing end of said disposable sensor such that said electrodes are in electrical contact with said capacitance measurement circuit.

23. The device of claim 22, wherein said disposable sensor is a plastic card.

24. The device of claim 23, wherein said test chamber, said power source, said measure and said disposable sensor are characterized by being suitable for self-operation by a lay person.

25. The device of claim 22, wherein said first and said second pairs of electrodes share a common electrode.

26. The device of claim 22, wherein said at least one pro-coagulating factor is dried onto said disposable sensor.

27. The device of claim 22, wherein said at least one pro-coagulating factor is a liquid droplet placed onto said disposable sensor.

28. The device of claim 22, wherein said clotting time is determined as a prothrombin time.

29. The device of claim 22, wherein said clotting time is determined as a partial prothrombin time.

30. The device of claim 1, wherein said electrodes are constructed from a material selected from the group consisting of carbon, graphite and metal.

31. The device of claim 30, wherein said material is a carbon, graphite or metal impregnated film.

32. The device of claim 30, wherein metal is in a form selected from the group consisting of film, foil, metal impregnated film and metal sputtered film.

33. The device of claim 32, wherein said metal is selected from the group consisting of silver, titanium, stainless steel, palladium, copper and a mixture of silver and silver chloride.

34. The device of claim 1, wherein said electrodes extend along substantially the entirety of said test chamber.

35. The device of claim 1, wherein said electrodes are disposed on opposing sides of said test chamber.

36. The device of claim 1, wherein said electrodes extend along a portion of said test chamber, a length of said portion being shorter than a length of said test chamber.

37. The device of claim 36, wherein said electrodes are disposed on opposing sides of said test chamber and a first electrode of said electrodes is on a side nearer an entrance of said test chamber than a second electrode of said electrodes, such that the viscosity of the sample of liquid is determined by a period of time required for the sample to travel from said first electrode to said second electrode, such that a capacitance is measurable substantially only when the sample occupies substantially all the area located between both said first electrode and said second electrode.

38. The device of claim 1, wherein said chamber features a plurality of surfaces, and said plurality of surfaces is pretreated.

39. The device of claim 38, wherein said pretreated surfaces are pretreated by being soaked in a buffer containing an ingredient selected from the group consisting of a detergent and a hydrophilic polymer.

40. The device of claim 1, further comprising:
 (e) a cover for covering said test chamber, said cover featuring at least one aperture.

* * * * *